Figure 1:
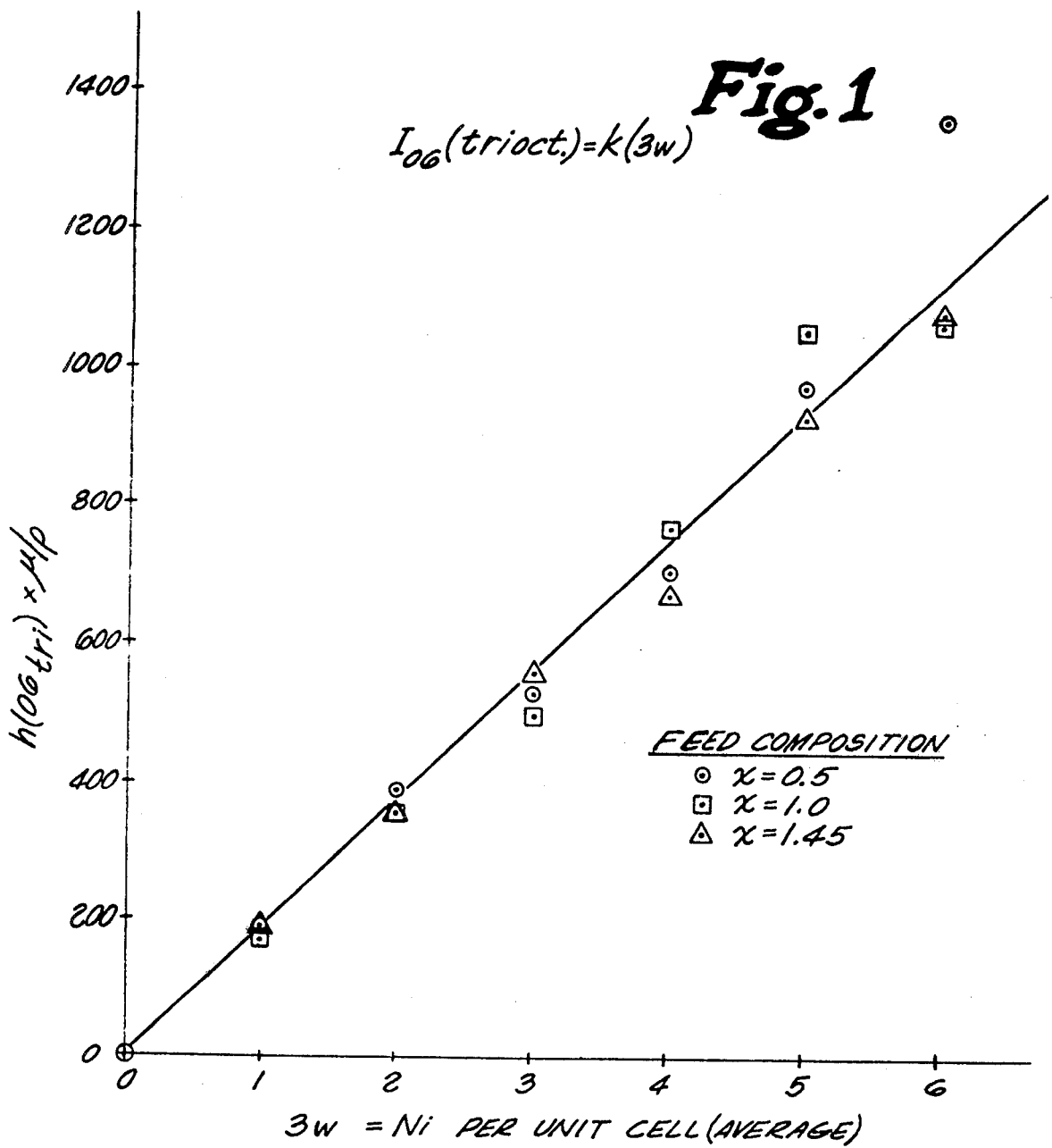

United States Patent [19]

Black et al.

[11] 4,022,684

[45] May 10, 1977

[54] HYDROCARBON CONVERSION PROCESS USING A NI AND/OR CO SUBSTITUTED SYNTHETIC ALUMINOSILICATE CATALYST

[75] Inventors: Edgar R. Black, Aspinwall; Angelo A. Montagna, Monroeville; Harold E. Swift, Gibsonia, all of Pa.

[73] Assignee: Gulf Research & Development Company, Pittsburgh, Pa.

[22] Filed: Apr. 26, 1976

[21] Appl. No.: 680,028

Related U.S. Application Data

[60] Division of Ser. No. 461,907, April 18, 1974, Pat. No. 3,966,642, which is a continuation-in-part of Ser. No. 441,059, Feb. 11, 1974, abandoned, which is a continuation-in-part of Ser. No. 291,263, Sept. 22, 1972, abandoned.

[52] U.S. Cl. .............................. 208/111; 208/215; 208/216; 252/442; 260/683.65; 260/683.68
[51] Int. Cl.² .................. C10G 13/08; C07C 5/30; B01J 27/12
[58] Field of Search ................. 208/111, 215, 216; 260/683.65, 683.68

[56] References Cited

UNITED STATES PATENTS

| | | | |
|---|---|---|---|
| 3,252,889 | 5/1966 | Capell et al. | 208/120 |
| 3,652,457 | 3/1972 | Jaffe | 252/442 |
| 3,803,026 | 4/1974 | Jaffe | 208/111 |
| 3,852,405 | 12/1974 | Granquist | 423/118 |
| 3,929,622 | 12/1975 | Granquist | 208/120 |

*Primary Examiner*—Delbert E. Gantz
*Assistant Examiner*—G. E. Schmitkons

[57] ABSTRACT

The conversion of hydrocarbons in the presence of hydrogen occurs under hydrocarbon conversion conditions in the presence of a subgroup of a certain class of metal-substituted semi-crystalline aluminosilicates which are synthetic and which are predominantly ordered in two directions, that is, which are laminar or have a layered or stacked sheet structure. The metal substituted for the aluminum in the trioctahedral sites is nickel, cobalt, or mixtures thereof. The catalysts are preferably used in hydroisomerization and hydrocracking processes.

41 Claims, 2 Drawing Figures

HYDROCARBON CONVERSION PROCESS USING A NI AND/OR CO SUBSTITUTED SYNTHETIC ALUMINOSILICATE CATALYST

RELATED APPLICATION

This is a division of application Ser. No. 461,907 filed Apr. 18, 1974 (now U.S. Pat. No. 3,966,642), which is a continuation-in-part of Ser. No. 441,059 filed Feb. 11, 1974 (now abandoned), which is in turn a continuation-in-part of Ser. No. 291,263 filed Sept. 22, 1972, now abandoned.

This invention relates to a hydrocarbon conversion process and to a catalyst therefor. More particularly, this invention relates to a process for the conversion of hydrocarbons in the presence of hydrogen using certain metal-substituted synthetic aluminosilicate minerals as catalysts.

The conversion of hydrocarbons in the presence of hydrogen to produce products of upgraded value is of special interest to the petroleum industry. Such processes represent, for example, the hydrocracking of furnace oils to produce high octane number gasoline, the hydrogenation of residuals to remove sulfur, the hydroisomerization of hydrocarbons such as straight-chain hydrocarbons to produce branched chain structures which are of higher octane number as gasoline components; the hydrocracking of raffinate hydrocarbons to form liquid petroleum gas; etc. It is particularly important that these reactions be performed efficiently, that is, with as little undesirable side reactions as possible. For example, in the hydrocracking of furnace oils to obtain high octane number gasoline, it is desirable to retain aromatics while reducing the boiling point of the charge stock into the gasoline range. It is also desirable to perform this hydrocracking operation at as low a temperature and pressure as possible. Many catalysts have been proposed in the prior art to perform the above type of hydrocarbon conversion reactions in the presence of hydrogen, but the prior art catalysts have certain undesirable characteristics associated with them, such as poor activity at low temperatures or the indiscriminate hydrocracking of aromatics when it is desirable that such aromatics be retained.

It has now been discovered in accordance with the invention that a subgroup of a certain class of metal-substituted semicrystalline aluminosilicates which are synthetic and which are predominantly ordered in two directions, that is, which are laminar or have a layered or stacked sheet structure, are highly active and selective hydrocarbon conversion catalysts. In accordance with the invention, a hydrocarbon type charge stock is reacted in the presence of hydrogen and in the contact presence of a catalyst comprising:

a laminar 2:1 layer-lattice aluminosilicate mineral possessing layer-lattice unit cells, each cell having an inherent negative charge balanced by cations exterior to said unit cell, said mineral corresponding to the following overall formula prior to drying and calcining:

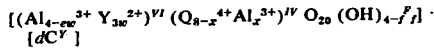

where
Al is aluminum;
Y is selected from the class consisting of nickel, cobalt and mixtures thereof;
Q is at least 0.95 mol fraction silicon ions, the remainder consisting of tetravalent ions having an ionic radius not to exceed 0.65 A;
F is fluorine;
C is at least one charge-balancing cation; and
where
$e$ has a numerical value from 2 to 3 inclusive;
$w$ has a numerical value from 0.01 to 2 inclusive, with the proviso that the quantity $ew$ have a numerical value from 0.02 to 4 inclusive;
$f$ has a value of 4 or less;
$x$ has a numerical value from 0.05 to 2.0 inclusive;
$y$ is the valence of the cation C; and
$d$ is the number of cations C where the product $dy = x + 3(e-2)w$.

In the above formulation, the first bracket represents the overall average laminar layer-lattice unit cell structure formulation, which, as will be explained hereinbelow, possesses an inherent negative charge by reason of the fact that the positive charges of the cations are less than the negative charges of the anions. Since the preparation as a whole is electrostatically neutral, the charge-balancing cations which are necessarily present are external to the lattice and are represented by the second bracket, in which C stands for the charge-balancing cations taken as a whole, with $y$ being their average charge and $d$ being the number of charge-balancing cations per unit cell. It will be recognized that in this formulation, C may actually correspond to a large variety of charge-balancing cations simultaneously present, such as, for example, a mixture of hydrogen, calcium and the like cations. For catalytic purposes, it is preferred that the mineral be free of alkali metals which can occur in the exchange sites (C) due to the presence of alkali metals, for example, in the preparative solutions. Minor amounts of alkali metals, such as 5 to 10% of the exchange sites, or as much as 35% of the exchange sites, can be tolerated.

It is clear from the formulation given that Y consists of divalent nickel or cobalt ions either isomorphously substituted for a like number of aluminum ions, whereby a charge deficit results, or substituted on the basis of three divalent ions for two aluminum trivalent ions with no resulting charge deficit, or a mixture of both. In like manner, it is clear that Q, while consisting predominantly of silicon ions, may include a minor proportion of tetravalent ions isomorphously substituted for some of the silicon ions without affecting the overall charge; while trivalent aluminum ions in a proportion represented by subscript $x$ are isomorphously substituted for a like number of silicon ions, whereby a charge deficit results from the substitution of a trivalent ion for a tetravalent ion.

For the sake of convenience, a tabulation follows in which the Y and Q elements usable in accordance with the invention are listed. It will be clear that this listing results from checking each element against its known valence states and its known ionic radius for each applicable valence state, taking into account the coordination number where the latter affects the ionic radius. Tables of ionic radii for various elements have appeared in the literature during the last half century, and in the case of disparity among the values given for a specified element, the best value has been chosen in the light of all of the known data, and this best value is the one which appears in the tables which follow.

TABLE A

| Y: Divalent - Maximum 0.75 A | | |
|---|---|---|
| Nickel | (Ni) | 0.69 |
| Cobalt | (Co) | 0.72 |

TABLE B

| Q: Tetravalent - Maximum 0.65 A | | |
|---|---|---|
| Silicon | (Si) | 0.41 |
| Germanium | (Ge) | 0.53 |

Preferably, in the above unit cell formula, Q is silicon. Further, the value of $e$ is preferably about 2; the value of $w$ from 0.2 to 1.66 with the value of $ew$ being preferably from 0.4 to 3.32. The value of $x$ is preferably from 0.5 to 2, and the value of $f$ is preferably from 0.5 to 3.75.

Moreover, usually, although not necessarily, the composition of the charge-balancing cations in the second bracket contains some proportion of the partial hydroxides of aluminum. Thus, in accordance with a more particular formulation, the composition of the charge-balancing cations in the second bracket contains some proportion of the partial hydroxides of aluminum. Thus, in accordance with a more particular formulation, the composition of the charge-balancing cations in the second bracket may conveniently be represented as follows:

$$[a\ M^n + b\ Al\ (OH)_{3-z}{}^z]$$

wherein $$an + bz = dy = x + 3(e-2)w$$

and M is at least one charge-balancing cation and is preferably selected from the group consisting of hydrogen; ammonium; substituted ammonium; substituted phosphonium; multivalent metal cations other than aluminum; and partial hydroxides of multivalent metal cations; and $n$ is the unsatisfied valence of M. In practice, the product $bz$ is a small value compared to the product $an$.

This second, more particular characterization of the charge-balancing cations is believed to correspond more closely to the products initially obtained in accordance with the preferred mode of preparation. Moreover, it provides explicitly for any hydroxyaluminum cations which may be present. It will be understood that such hydroxyaluminum cations are commonly present as a mixture of species, as described, for example, in U.S. Geological Survey Water-Supply Paper 1827-A (1967), which is incorporated herein by reference. However, since these charge-balancing cations are essentially exchangeable without disturbing the lattice itself, the latter being represented by the first bracket, after having made a given preparation in accordance with the invention by a preferred procedure, it is relatively simple to exchange a portion of the cations represented by M or indeed substantially all of the cations represented by M in the second bracket for some other preselected cation or mixture of cations. The partial hydroxides of aluminum are exchangeable with difficulty, if at all. Thus, for example, referring to the first general formulation given hereinabove, the charge-balancing cation C can at will be selected from such diverse species as palladium, hydroxyaluminum, hydroxynickel, trimethylammonium, alkyl phosphonium, and the like cations and indeed mixtures thereof. Thus, C may be selected from the group consisting of alkaline earth metal, heavy metal, heavy metal partial hydroxides, ammonium, substituted ammonium, substituted phosphonium, and the like cations and mixtures thereof. As noted above, alkali metals are preferably excluded but may be present in minor amounts.

In the case of the use of substituted ammonium and substituted phosphonium ions and the like, the substitutents should be such that they can be driven off during calcination of the mineral.

Those skilled in the art will recognize, accordingly, that the first bracket of the above formula relates to a fixed array of ions in a tripartite lamina which for convenience may be described as muscovite-like, and in which the positive ions shown in the first parentheses are in octahedral coordination with sheets comprising oxygen, hydroxyl, and fluoride ions; whereas the positive ions shown in the second parentheses in the first bracket are in tetrahedral coordination jointly with the aforesaid sheets of oxygen, hydroxyl, and fluoride ions, and also with sheets of oxygen ions in essentially a hexagonal ring array constituting the external faces of the tripartite lamina. The positive ions shown in the second bracket have no essentially fixed position, but are in effect external to the lattice of the tripartite lamina.

Those skilled in the art will also recognize that when some of the parameters in the above formulations have values outside of the stipulated ranges, the formulations reduce to representations of various end members of a broad group of laminar aluminosilicates, which of course are outside of the scope of the present invention. Thus, for example, when $w$ and $x$ both equal zero, and no fluoride ion is present, the first bracket describes the mineral pyrophyllite. It will also be seen that the factor $d$ is equal to zero, when $w$ and $x$ equal zero, so that the ionic species set forth in the second bracket are not present, which of course results from the fact that the lattice of pyrophyllite is charge-balanced. Again, for the case in which $x$ equals zero, $w$ equals two, $e$ equals two, and no fluoride is present, a mineral results in which the lattice is likewise charge-balanced, and the ionic species set forth in the second bracket are not present. Such a mineral is described in U.S. Pat. No. 2,658,875 to Cornelis et al.

In general, 2:1 layer-lattice aluminosilicate minerals, or in alternative nomenclature, tripartite aluminosilicate minerals of the type concerned in the present invention, may be classified as either dioctahedral or trioctahedral, depending upon whether the number of cations per unit cell in the octahedral (or inner) layer is approximately 4 or 6, respectively. The foregoing structural formula is, as stated, an overall formula for a given preparation, and the fact that the number of such octahedral cations may vary from 4 to 6 in a continuous manner in the formulation given does not mean that a single lamina is present having such an intermediate number of cations. In point of fact, the individual laminae are believed to be either dioctahedral or trioctahedral, and in a given preparation the relative proportions of the dioctahedral and trioctahedral species will give rise to the numerical values obtained in quantitatively characterizing the preparation in accordance with the foregoing formula. Where $e$ in the formulation is intermediate between 2 and 3, accordingly, both 1:1 and 3:2 substitutions are present. Because of the extremely small particle size of the minerals, the exact physical nature of these mixed phase systems is uncertain. In any case, in this specification, the term "a mineral" shall mean the 2:1 layer lattice products which are produced by simultaneously synthesizing both the dioctahedral and trioctahedral phases in place in a single reaction mixture. It may be emphasized that such mineral made for use in this invention is a single mineral species, even though it may contain two phases. The minerals of this invention, therefore, differ significantly from compositionally similar mixtures obtained by simply mixing together the separately synthesized dioctahedral and trioctahedral members.

The minerals in accordance with the invention are synthesized by a hydrothermal route, detailed examples of which will be given later. The procedure follows in a general way that set forth in U.S. Pat. No. 3,252,757 to W. T. Granquist, except that the cited patent does not relate to the inventive aluminosilicates, which contain additional elements, so that the reaction mixtures required in the present invention are substantially different. As will be evident from the structural formula already given, the reaction mixture for the hydrothermal synthesis includes a source of one or more multivalent cations other than aluminum and silicon. For example, for the case of nickel, this may be a relatively soluble compound, such as, for example, nickel acetate, nickel fluoride, nickel nitrate, and the like; or it may be a relatively insoluble nickel compound such as nickel hydroxide. It is of interest that in general the inclusion of soluble nickel salts in the reaction mixture tends to cause the nickel to occur predominantly in the trioctahedral phase, while relatively insoluble nickel compounds promote its occurrence in the dioctahedral phase. The terms are well understood in the art, and a brief explanation in addition to that already given may be found on page 156 of the book by George Brown, "The X-Ray Identification and Crystal Structures of Clay Minerals", London 1961. The classical paper by Ross and Hendricks, "Minerals of the Montmorillonite Group", U.S. Geological Survey Professional Paper 205-B (1945) is helpful, particularly for its treatment of variation of the members of a given series of laminar aluminosilicate minerals.

For the other elements useful in practicing the invention, such as cobalt, the most commonly available simple inorganic and organic compounds thereof may in general be used, as will be evident to those skilled in the art.

The minerals after their preparation are activated for use as catalysts by drying and calcining. By drying is meant the removal of the external water of absorption by heating. Usually the drying temperatures are from 250° to 350° F. at atmospheric pressure, albeit higher and lower pressures can, of course, be employed. By calcining is meant the addition of heat to effect some chemical change in the catalyst such as the removal of chemically bound water or ammonia if the charge-balancing cation is $NH_4^+$. The calcining temperatures are normally from about 800° F. to about 1300° F. Atmospheric pressure is usually employed but higher or lower pressures can, of course, be used. The maximum calcination temperature should be below that temperature wherein a phase inversion may occur. Thus, dehydration of the dioctahedral phase may preferably occur at normal calcination temperatures but increased temperatures tend to result in dehydration of the trioctahedral phase which may then recrystallize to form a new undesired mineral species. Minor amounts of ammonium, substituted ammonium, etc. type ions which can be changed during the drying and calcining cycle may remain. Usually C in the above formula after drying and calcining is selected from the group consisting of $H^+$, a multivalent metal cation or the partial hydroxide of a multivalent metal cation.

The heat activated minerals are suitable in accordance with the invention as catalysts for the conversion of hydrocarbon charge stocks in the presence of hydrogen but these materials tend to age more quickly than desired. In accordance with another aspect of this invention, an improved catalyst comprises the minerals described above containing, in addition, a hydrogenation component deposited thereon. Any suitable hydrogenation component can be employed. For example, a suitable hydrogenation component would be one or more metals from Groups VI and/or VIII of the Periodic Table. These metals or combinations of metals are deposited on the heat activated minerals described above and do not form a part of the mineral structure as do the Y and Q defined metals. The deposited metals can be in the form of metals, metal sulfides or metal oxides or mixtures thereof.

The method of deposition of the hydrogenation component is not critical and any method well knwon in the art can be employed, such as, for example, the deposition of the hydrogenation component onto a dried or heat activated mineral from a solution of the aqueous salts of the metals. The technique of minimum excess solution can suitably be employed, or an aqueous solution of the desired metal, such as palladium nitrate, can be added to an aqueous slurry of the formed mineral without intermediate drying or calcining. The hydrogenation component can also be added using techniques known in the art for exchanging metal ions with solid inorganic exchanges, such as zeolites. Also, the hydrogenation component can be added as a result of the reaction of a metal salt with the base material especially when $[dC^v]$ is $H^+$ or $NH_4^+$. For example, if $NiCl_2$ is intimately mixed in the dry state with the hydrogen form of the base material, and then heated, HCl can be evolved with the result that Ni is dispersed uniformly throughout the structure.

After the deposition of the hydrogenation component, the composition is suitably activated by drying under the usual conditions following by calcining, again under the usual conditions.

The preferred hydrogenating components are nickel, cobalt and the platinum group metals, and in particular palladium.

The amount of the hydrogenation component will depend somewhat on the metal or combination of metals chosen. The platinum group metals are usually used in a concentration of 0.01 to 5 weight percent of the final catalyst, usually from 0.10 to 1.0 weight percent. The other metals from Groups VI and VIII are normally used in higher concentrations on the order of 0.2 to 20 weight percent.

For ease of discussion, the following description will refer to nickel, but it is to be understood that any metal or mixture of metals included within the definition of Y is meant.

Figure 2:
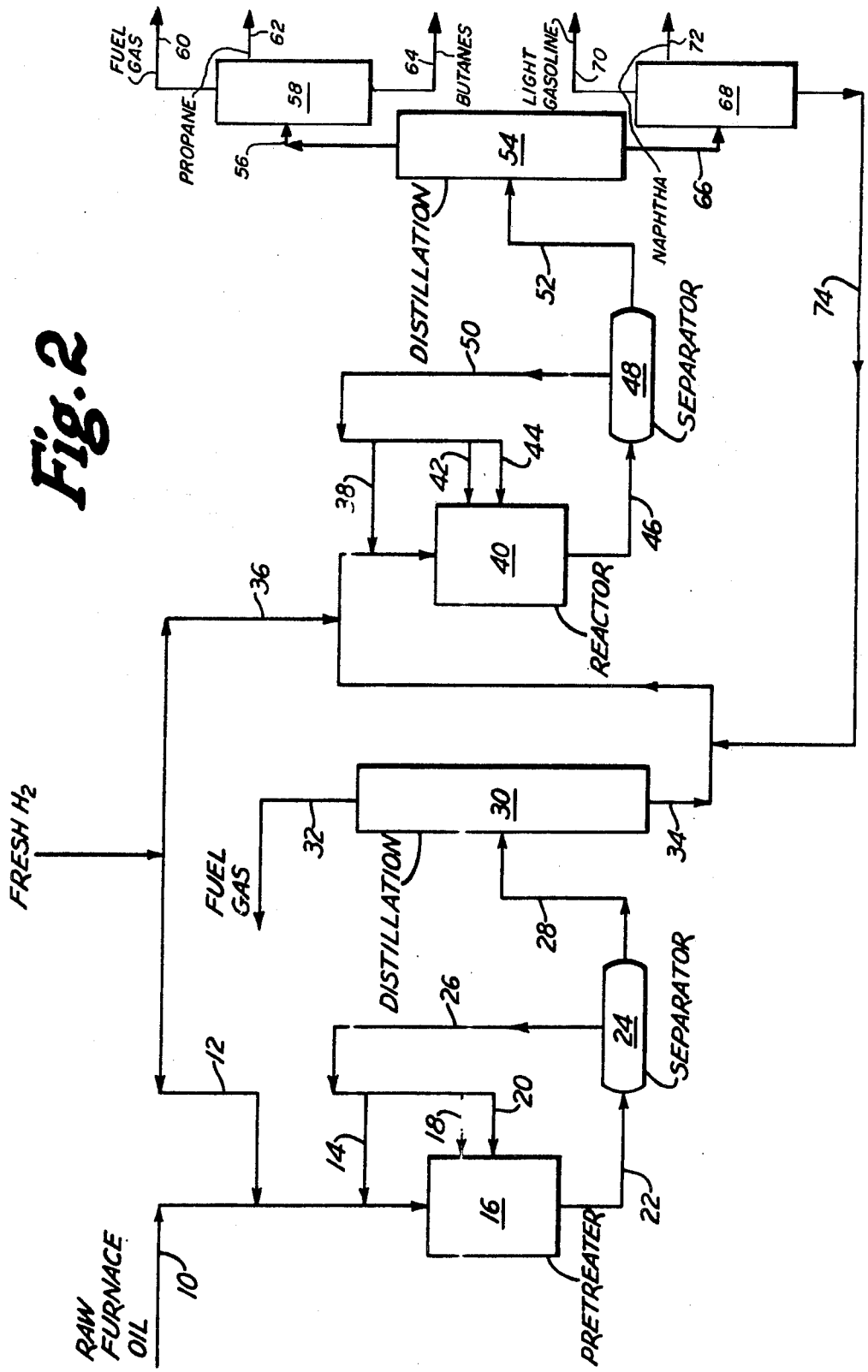

Two sheets of drawings consist of FIGS. 1 and 2. In FIG. 1 are plotted diffraction data showing the 06 reflections as a function of the Ni concentration per unit cell. FIG. 2 is a flow diagram of a preferred scheme for the hydrocracking of a furnace oil to produce a high quality naphtha.

Some specific examples of the synthesis of minerals will now be given. From these examples, the general procedure will be clear, and it may be noted that if one desires a higher or lower ratio of nickel to silicon, or a higher or lower ratio of aluminum to silicon in the final product, the relative proportions of these components in the reaction mixture should be adjusted accordingly.

EXAMPLE 1

346 g. of hydrated alumina, $Al_2O_3\cdot3H_2O$ (Alcoa C 31, 64.9% $Al_2O_3$) were added with stirring to a polysilicic acid sol which was prepared by passing sodium silicate solution over a hydrogen-resin. The volume of sol was chosen so as to contain 317 g. $SiO_2$. 8.95 g. of $NH_4F\cdot HF$ were then dissolved in this silica-alumina slurry. In a separate vessel, 19.1 g. of $NiF_2\cdot4H_2O$ were dispersed in 63.0 g. of an ammonium hydroxide solution assaying 58.8% $NH_4OH$. This ammoniacal slurry was then added to the silica-alumina dispersion, with stirring. If gel formation occurred, sufficient water was added to break the gel so that efficient stirring could continue. The final feed slurry, with a pH 8.5, was charged to a 1-gallon stirred autoclave, heated quickly (1 to 1½ hr.) until pressure line-out at 1240 psig (300° C.) and maintained at this temperature and pressure for three hours. The product was cooled in the pressure vessel, removed, sheared in a blender to insure homogeneity, and a small quantity dried for analysis. The product slurry had a pH = 7.4. The dried sample had a total nickel content of 1.30% (as Ni); the non-exchangeable Ni content was 1.2%. The sample gave an X-ray diffraction pattern typical of 2:1 layer-lattice silicates.

Pd was placed on the clay by adding to 1535 g. of product slurry a solution which contained 4.185 g. of $(NH_4)_2PdCl_4$ dissolved in 125 ml of deionized water. The slurry was stirred (with mild agitation) overnight at room temperature, and then filtered. The filter cake was washed twice by redispersion in deionized water and refiltrated. The final filter cake was air-dried at 110° C., cooled, and crushed to 10/20 mesh particles. The final catalyst contained 1.4% Ni and 0.8% Pd.

EXAMPLE 2

This synthesis was similar to Example 1, described above, except that the proportions of the starting materials were altered to yield a clay of approximately 10% Ni content. The feed slurry was composed of 2890 g. of polysilicic acid sol (which contained 5.2% $SiO_2$), 164 g. $Al_2O_3\cdot 3H_2O$, 95.5 g. $NiF_2\cdot4H_2O$ and 42.7 g. of $NH_4OH$ solution (which contained 47% $NH_4OH$). The feed and product pH were 8.4 and 8.5, respectively. The total nickel content of the product was 11.1% (as Ni); the non-exchangeable nickel content was 9.9%. Pd was added as previously described; the finished catalyst contained 10.1% Ni and 0.8% Pd.

EXAMPLE 3

25 pounds of $SiO_2$ (as polysilicic acid sol assaying 5.2% $SiO_2$) were pumped into a feed mix tank equipped with an efficient high-torque stirring system. To this silica sol were added with stirring 27.3 pounds commercial trihydrate of alumina (which assayed 64.9% $Al_2O_3$), 23.5 pounds of nickel acetate.4-hydrate (which contained 23.7% Ni) previously dissolved in 10 gal $H_2O$ and 1.24 pounds of $NH_4F\cdot HF$ (purity of 96%) already in solution in 1 gal $H_2O$. With continued stirring, sufficient aqua ammonia was added to bring the slurry pH to 8. This pH adjustment was accomplished with 13 pounds of aqua ammonia, which contained 48% $NH_4OH$. The final volume of slurry was about 75 gal.

After approximately 10 hr. of agitation, the feed slurry was pumped into a 100 gal jacketed autoclave, heated by electric heaters immersed in Dowtherm. The alutoclave was sealed and heating started. After 12 hr.—45 min., temperature lined out at 300° C. and a pressure of 1240 psig. The contents were maintained at these conditions for 4 hours at which time drawdown through a quench condenser and expansion valve was started. Total time for discharge was 1 hour. A small sample was dried, examined and found to be a 2:1 layer-lattice aluminosilicate which contained 9.6% Ni. A portion of the product was retained as slurry for after-treatment by Pd impregnation as previously described.

EXAMPLE 4

143.5 g. of hydrated alumina, $Al_2O_3\cdot3H_2O$ (Alcoa C 31, 64.9% $Al_2O_3$) were added with stirring to a polysilicic acid sol which was prepared by passing sodium silicate solution over a hydrogen-resin. The volume of sol was chosen so as to contain 150 g. of $SiO_2$. 7.43 g. of $NH_4F\cdot HF$ were then dissolved in this silica-alumina slurry. 94.5 g. of $Ni(Ac)_2\cdot4H_2O$ were dissolved in a minimum amount of water, added to the above slurry, and 29.8 g. of aqua ammonia (assaying 58.8% $NH_4OH$) were added with stirring. If gel formation occurred, sufficient water was added to break the gel so that efficient stirring could continue. The proper volume of the final feed slurry was charged to a one-gallon stirred autoclave, heated quickly (1 to 1½ hrs.) until the pressure lined out at 1250 psig (300° C.) and was maintained at this temperature and pressure for 3 hours. The product was cooled in a pressure vessel, removed, sheared in a blender to insure homogeneity and dried at about 250° F. Palladium was added to the dried product by impregnation in the same manner as described in Example 1, and the final catalyst contained 6.75% Ni and 0.56% Pd.

EXAMPLE 5

Example 4 was repeated except using 131 g. of hydrated alumina, 120 g. of $SiO_2$, 5.68 g. of $NH_4F\cdot HF$, 130 g. of aqua ammonia and 113 g. of cobalt acetate $(Co(Ac)_2\cdot4H_2O)$ in lieu of nickel acetate. The final catalyst contained 7.36% cobalt and 0.64% palladium.

While the products are somewhat well crystallized, the actual size of the crystal does not lend itself readily to characterization by the older methods of optical crystallographic methods. Much more precise are the results obtained by X-ray diffraction, and by way of further characterization of the products in accordance with the invention, there follow tabulations of spacings and intensities obtained on a number of mineral products having chemical compositions embraced by the earlier formula. Tables I–IV inclusive show such X-ray diffraction data for two series of products made along the lines indicated in Examples 1–4 inclusive.

The products tabulated in Table I consist, except at the end members, of mixed di- and trioctahedral phases. The Ni-free end member is "pure" dioctahedral; the Ni$_6$ sample is pure trioctahedral. In the intermediate range, the amount of trioctahedral phase increases with the Ni/unit cell. The products summarized in Table III are pure trioctahedral.

In the series shown in Tables I and II, the aluminum (IV) content was held constant at one and one-half atoms per unit cell while the nickel content was varied from zero to six atoms per unit cell. A summary of the results obtained is given in Table I with a more detailed tabulation following in Table II. It will be understood that the first number of this series, in which no nickel is present at all, is outside of the scope of the invention; the results are shown merely for comparative purposes.

In the series for which results are given in Tables III and IV, the nickel content was held constant at six atoms per unit cell, while the tetrahedral aluminum was varied from zero to two atoms per unit cell. Here again, the first number of the series, containing no aluminum, is outside of the scope of this invention and the results are included in the tabulation for comparative purposes. Table III is a summary, and Table IV shows the results in detail for each member of the series.

TABLE I

SUMMARY
Ni VARIABLE, x = 1.5
d, A (d spacings in A)

| Ni/u.c. | 0 | ⅛ | 1 | 2 | 3 | 4 | 5 | 6 |
|---|---|---|---|---|---|---|---|---|
| Index* | | | | | | | | |
| 001 | | | | | | | | |
| 001 | 10.6 | 11.8 | 11.3 | 11.3 | 13.0$^b$ | 13.4$^b$ | 13.4$^b$ | 13.6$^b$ |
| 002 | 5.18 | 5.68 | 5.34 | 5.24 | — | — | — | — |
| 003 | 3.41 | 3.26 | 3.37 | 3.34 | — | — | — | — |
| 004 | — | — | — | — | 3.30 | 3.26 | 3.24 | 3.29 |
| 005 | 2.061 | 2.065 | — | — | — | — | — | — |
| hk | | | | | | | | |
| 11;02 | 4.46 | 4.46 | 4.50 | 4.48 | 4.48 | 4.50 | 4.55 | 4.54 |
| 13;20 | 2.57 | 2.56 | 2.58 | 2.57 | 2.58 | 2.58 | 2.61 | 2.58 |
| 31;15;24 | 1.691 | 1.687 | 1.699 | 1.67 | 1.691 | — | — | — |
| 06 | 1.499 | 1.492 | 1.517 / 1.502 $^a$ | 1.522 / 1.502 $^a$ | 1.520 / 1.500 $^a$ | 1.522 | 1.524 | 1.522 |
| khl | | | | | | | | |
| 131 (Prob.) | 2.453 | 2.45 | 2.453 | 2.42 | 2.466 | 2.47 | — | 2.51 |

*Significant peaks only. See detailed tables for intensity data. Basal sequence may involve mixed layering. If so, indices would be mixed; e.g. 003/004.
$^a$Doublet consisting of di- and trioctahedral components.
$^b$Probably intercalated acetate.

TABLE II(a)

Ni VARIABLE, x = 1.5 (EXPECTATION VALUE)$^a$
Ni = ⅛ u.c.

| d, A | Probable Index | Height, mm | Comment |
|---|---|---|---|
| 11.8 | 001/001 | 172 | Strong, Symmetrical |
| 5.68 | 002/002$^c$ | 18 | Weak, Symmetrical |
| 4.46 | 11;02 | 148 5.5 mm, w/2$^b$ | Strong, Asymmetrical |
| 3.26 | 003/004 | 48 | Symmetrical |
| 2.56 | 13;20 | 65 | Asymmetrical (band, 2.31–2.62) |
| 2.45 | hk | 36 | Shoulder |
| 2.065 | 00l$^c$ | 18 | Symmetrical |
| 1.687 | 31;15;24 | 20 | Asymmetrical |
| 1.492 | 06 | 42 12 mm, w at h$^d$/2 | Slightly Asymmetrical |

$^a$Expectation Value in this and other Tables means the value of x based on the starting compositions.
$^b$w/2 in this and other Tables means half-width at baseline. For asymmetrical peak, smaller distance.
$^c$Uncertain due to complications due to mixed layering.
$^d$w at h/2 in this and other Tables means half-height.

TABLE II(b)

Ni = 1/u.c.

| d, A | Probable Index | Height, mm | Comment |
|---|---|---|---|
| 11.32 | 001/001 | 140 | Strong, well defined |
| 5.34 | 002/002 | 11 | Weak, Symmetrical |
| 4.50 | 11;02 | 147 7.5 mm, w/2 | Asymmetrical, Sharp |
| 3.37 | 003/004$^a$ | 47 | Symmetrical, Broad |
| 2.583 | 13;20 | 102 | Asymmetrical, Mod. sharp |
| 2.453 | hk | 56 | Symmetrical |
| 1.699 | 31;15;24 | 17 | Asymmetrical, Broad |
| 1.517 / 1.502 | 06 | 22 / 48 | (Doublet - 1.517 is a shoulder on low-angle side of 1.502 |

$^a$Uncertain due to complications due to mixed layering.

TABLE II(c)

Ni = 2/u.c.

| d, A | Probable Index | Height, mm | Comment |
|---|---|---|---|
| 11.32 | 001/001 | 135 | Not well defined |
| 5.24 | 002/002 | 6 | Symmetrical |
| 4.48 | 11;02 | 122 6 mm, w/2 | Strong, sharp, asymmetrical |
| 3.34 | 003/004 | 40 | Symmetrical, broad |
| 2.57 | 13;20 | 93 | Asymmetrical, Mod. sharp |
| 2.42 | hk | 55 | Asymmetrical |
| 1.67 | 31;15;24 | 13 | |
| | 06 | 35 | |
| 1.522 / 1.502 | | 35 | Doublet - about equal height; trioct. dioct. |

TABLE II(d)

Ni = 3/u.c.

| d, A | Probable Index | Height, mm | Comment |
|---|---|---|---|
| 13.0 | 001/001$^a$ | 190 | May have intercalated acetate |
| 4.48 | 11;02 | 90 11 mm, w/2 | Asymmetrical |
| 3.30 | 003/004$^a$ | 40 | Broad, symmetrical |
| 2.576 | 13;20 | 96 | Mod. sharp asymmetrical |
| 2.466 | hk | 61 | Ill-defined |
| 1.691 | 31;15;24 | 15 | Broad |

TABLE II(d)-continued

Ni = 3/u.c.

| d, A | Probable Index | Height, mm | Comment |
|---|---|---|---|
| 1.520 ⎫<br>1.500 ⎭ | 06 | 53 | Doublet - 1.500 A a shoulder on high angle side of 1.520 trioct. |

*Uncertain due to complications due to mixed layering.

TABLE II(e)

Ni = 4/u.c.

| d, A | Probable Index | Height, mm | Comment |
|---|---|---|---|
| 13.4 | 001/001* | 201 | Ill-defined - may have intercalated acetate |
| 4.50 | 11;02 | 56 14 mm, w/2 | Asymmetrical |
| 3.26 | 00 | 38 | Broad, symmetrical |
| 2.58 | 13;20 | 86 | Asymmetrical |
| 2.47 | hk | 58 | Broad shoulder on 2.58 |
| 1.522 | 06 | 67 | Asymmetrical - tailing toward high angle side |

*Uncertain due to complications due to mixed layering.

TABLE II(f)

Ni = 5/u.c.

| d, A | Probable Index | Height, mm | Comment |
|---|---|---|---|
| 13.4 | 001 | 200 | Uncertain height - not well defined |
| 4.55 | 11;02 | 58 9 mm, w/2 | Asymmetrical |
| 3.24 | 00 | 45 | Symmetrical |
| 2.61 | 13;20 | 90 | Asymmetrical - band head band extends 2.64 1.97 A |
| 1.524 | 06 | 87 | Asymmetrical - tails toward high angle side |

TABLE II(g)

Ni = 6/u.c.

| d, A | Probable Index | Height, mm | Comment |
|---|---|---|---|
| 13.6 | 001* | 192 | Poorly defined - may be intercalated acetate |
| 4.54 | 11;02 | 59 9 mm w/2 | Asymmetrical |
| 3.29 | 004* | 40 | Very broad, symmetrical |
| 2.58 | 13;20 | 83 | Broad, band-head of band extending from 2.64 to 1.97 A |
| 2.51 | hk | 84 | Part of above band |
| 1.522 | 06 | 98 14 mm, width at h/2 | Mod. sharp asymm. tailing to high angle side |

*Uncertain

TABLE III

SUMMARY
Ni = 6, x = VARIABLE

| Al$^{IV}$/u.c. | 0 | ½ | 1 | 1.5 | 2 |
|---|---|---|---|---|---|
| Index* | | | | | |
| 00̄1 | | | | | |
| 001 | 9.6 | 11.6 | 13.4* | 13.6 | — |
| 002 | — | — | — | — | — |
| 003 | 3.145 | — | — | — | — |

TABLE III-continued

SUMMARY
Ni = 6, x = VARIABLE

| Al$^{IV}$/u.c. | 0 | ½ | 1 | 1.5 | 2 |
|---|---|---|---|---|---|
| 004 | — | 3.25 | 3.32 | 3.29 | 3.42 |
| 005 | — | — | — | — | — |
| hk | | | | | |
| 11;02 | 4.55 | 4.55 | 4.56 | 4.54 | 4.53 |
| 13;20 | — | 2.62 | 2.59 | 2.58 | 2.62 |
| 22;04 | 2.27 | — | — | — | — |
| 31;15;24 | — | — | — | — | — |
| 06 | 1.522 | 1.522 | 1.524 | 1.522 | |
| hkl | | | | | |
| 1̄31 (Prob) | 2.51 | — | — | 2.51 | 2.51 |

*Significant peaks only. See detailed tables for intensity data.
Basal sequence may involve mixed-layering. If so, indices would be mixed; e.g., 003/004. Also, possible intercalation of acetate may affect 001.
*This particular sample, when oriented and glycol treated, gave an 001 of 17.7 A.

TABLE IV(a)

Ni = 6, x = 2.0 (Expectation Value)

| d, A | Probable Index | Height, mm | Comment |
|---|---|---|---|
| 4.53 | 11;02 | 48.5 | Asymmetrical |
| 3.42 | 004* | 46 | Broad, symmetrical |
| 2.62 | 13;20 | 83 14 mm, w/2 | Very broad, part of band extending from 2.64 A 1.97 |
| 2.51 | hk | 85 | Very broad; part of same band |
| 1.526 | 06 | 78 16 mm at h/2 | Moderately sharp; slightly asymmetric |

NOTE:
001 is not defined; slight trade of kaolinite-like phase at 7.08 A.
*Uncertain.

TABLE IV(b)

x = 1.5 (Expectation Value)

| d, A | Probable Index | Height, mm | Comment |
|---|---|---|---|
| 13.6 | 001 | 192 | Poorly defined |
| 4.54 | 11;02 | 59 9 mm, w/2 | Asymmetrical |
| 3.29 | 004* | 40 | Very broad, symmetrical |
| 2.58 | 13;20 | 83 | Broad, part of band extending from 2.64 1.97 A |
| 2.51 | hk | 84 | |
| 1.522 | 06 | 98.5 14 mm w at h/2 | Moderately sharp; slightly asymmetric |

*Uncertain.

TABLE IV(c)

x = 1.0 (Expectation Value)

| d, A | Probable Index | Height, mm | Comments |
|---|---|---|---|
| 13.4* | 001 | 191 | Well defined on oriented slide; poorly defined on random slide |
| 4.56 | 11;02 | 61 11 mm, w/2 | Asymmetrical |
| 3.32 | 004* | 41 | Very broad, symmetrical |
| 2.59 | 13;20; | 83 | Asymmetrical band extending from 2.661 1.97 A |
| 1.524 | 90 90 14 mm, | Moderately sharp; w at h/2 | slightly asymmetric |

*Expanded to 17.7 A with glycol treatment
*Uncertain

TABLE IV(d)

x = 0.5 (Expectation Value)

| d, A | Probable Index | Height, mm | Comments |
|---|---|---|---|
| 11.6 | 001/001 | 224 | Strong, well defined |
| 4.55 | 11;02 | 81 7 mm, w/2 | Asymmetrical |
| 3.25 | 003/004 | 57 | Broad, symmetrical |
| 2.62 | 13;20 hk | 84 | Band-head listed Band extends 2.64 1.97 A, asymmetrical |
| 1.522 | 06 | 114 9 mm, w at h/2 | Sharp; slightly asymmetric |

TABLE IV(e)

x = 0

| d, A | Probable Index | Height, mm | Comments |
|---|---|---|---|
| 9.6 | 001 | 227 | Very strong, well defined, symmetrical |
| 4.55 | 11;02 | 97 8 mm, w/2 | Asymmetrical |
| 3.145 | 003 | 93 | Moderately sharp, symmetrical |
| 2.51 | 13;20 | 106) | Band (strongly asymmetrical |
| 2.27 | 22;04 | 47) | |
| 1.522 | 06 | 120 8 mm, w at h/2 | Sharp; slightly asymmetric |

From size considerations alone, $Ni^{2+}$ is expected to occupy octahedral sites and to be excluded from tetrahedral sites in the layer structure, or to occupy charge-balancing sites either as $Ni^{2+}$ or as a hydroxy-nickel species. $Al^{3+}$, however, can occupy octahedral, tetrahedral, or charge-balancing sites; in the latter case, a hydroxy-aluminum species is to be expected. The diffraction data in the previous tables shown 06 reflections typical of mixed dioctahedral/trioctahedral minerals. Furthermore, the trioctahedral 06 (>1.505 A) peak height increases, and the dioctahedral 06 (<1.505 A) decreases, as the overall average Ni per unit cell varies over the range 0 to 6. In addition, reference is made to the attached FIG. 1 wherein the intensity of the trioctahedral 06, corrected for change in the mass absorption coefficient as Ni increases and Al decreases, is plotted as a function of the expected overall average level of Ni, i.e. the expected overall average Ni per unit cell based on feed composition. In FIG. 1, $h(06_{tri})$ is the 06 peak height in chart units; $\mu/\rho$ is the mass absorption coefficient in the "Ni per unit cell (average)" to $3w$ as defined in the formula. Note the intensity is a linear function of the amount of Ni per unit cell and that the line extrapolates to zero intensity at zero nickel level. The equation for the intensity of the 06 line of the trioctahedral phase (I06(trioct)) is given on FIG. 1 as equal to $k(3w)$ where $k$ is a constant. The curve in FIG. 1 is the best fit for values of $x$ from 0.5 to 1.45. For this particular system, any amount of nickel added (within the compositional limits) crystallizes as a trioctahedral nickel silicate which may or may not contain 4- coordinated Al. Thus, in this system, any mixture of NiO and $Al_2O_3$ which contains less than the amount of Ni required for 6 Ni per unit cell will form mixed dioctahedral-trioctahedral phases.

It will be helpful to outline a procedure by which it may be determined if a given preparation falls within the scope of the claimed minerals before drying and calcining.

First, x-ray diffraction must establish the material in question to be a 2:1 layer silicate by procedures well known to those skilled in the art. Of particular help in this instance would be pertinent subject matter in the text by G. Brown, cited hereinabove. The material being examined should be substantially free of accessory phases.

It is then necessary to obtain a total analysis of the sample, expressed as the oxides of the cations in their original oxidation states. Suitable analytical methods are discussed in Furman, N. H., Ed. "Scott's Standard Methods of Chemical Analysis", 6th Ed. Van Nostrand, New York (1962), Vol. I, Chapter 41. If fluoride is present, the percent oxides plus percent fluoride is corrected by subtracting the percentage of fluoride ion multiplied by quotient of the equivalent weight of oxygen ion divided by the equivalent weight of fluoride ion. Adequacy of the analysis is indicated if this corrected total lies between 99.5% and 100.5%. The analysis is recalculated as charge equivalents (i.e., cation equivalents $x$ cation charge), normalized to charges per 44 charges (the negative charge per unit cell of the oxygen-hydroxyl framework of the 2:1 layer silicates) and finally expressed as cations per unit cell (e.g., the silicon charges per 44 charges divided by the charge of the silicon cation). These cations are then distributed over the tetrahedral and octahedral layers in accord with the tabulated lists of cations falling into the categories Y and Q. In this way the values of the various subscripts in the general formula can be obtained. Examples of this technique, a statement of the rules for cation distribution, and a discussion of the uncertainties involved and the meaning of the results can be found in Kelly, W. P., "Interpretation of Chemical Analyses of Clays", Clays and Clay Technology, Bulletin 169 of the California Division of Mines (1955), pp. 92–94; and Osthaus, B.B., "Interpretation of Chemical Analyses of Montmorillonite", same reference, pp. 95–100.

An illustrative example follows. This particular example has been selected to include the complexities arising from mixed di- and trioctahedral phases, mixed 1:1 and 3:2 substitution octahedrally, and mixed 4- and 6-fold coordinated aluminum ion.

Chemical analysis and charge data for a chosen mineral are summarized in Table C below:

TABLE C

| Component | Analysis | Cation Equiv. | Charge Equiv. | Charges per 44 Charges | Cations/ u.c. |
|---|---|---|---|---|---|
| $SiO_2$ | 50.59 | 0.842 | 3.37 | 27.59 | 6.90 |
| $Al_2O_3$ | 23.33 | 0.458 | 1.37 | 11.25 | 3.75 |
| NiO | 16.86 | 0.226 | 0.451 | 3.70 | 1.85 |
| $(NH_4)_2O$ | 4.61 | 0.177 | 0.177 | 1.45 | 1.45 |
| F | 2.09 | 0.110 | — | — | — |
| $H_2O$ | 3.41 | | | | |
| | 100.89 | | 5.369 | 43.99 | |
| F≡O[1] | −0.88 | | | | |
| Corr. Total | 100.01 | | | | |

[1]Fluoride equivalent to oxygen

Referring to the information in Table C, calculations can be made to show the distribution of cations in the tetrahedral and octahedral layers. All of the silicon is assumed to be in the tetrahedral layer and is equal to 6.90 cations per unit cell. Since there are 8 cations per unit cell in the tetrahedral layer, the number of aluminum cations per unit cell must be 1.10. It is also known that there are 32 charges in the tetrahedral layer. Because there is some $Al^{+3}$ in the tetrahedral layer rather than $Si^{+4}$, there is a net negative charge in the tetrahedral layer of 1.10. The aluminum distributed in the octahedral layer is calculated by difference to be 2.65 cations per unit cell, and the nickel by analysis is shown to be 1.85 cations per unit cell. Since it is known that the octahedral layer has 12 charges per unit cell, calculations show that the octahedral layer has a net negative charge of 0.35. The total net negative charge is 1.45, which is balanced by the interlayer $NH_4^+$ charge of 1.45 cations per unit cell to give an electrostatically neutral product.

From the tabulated calculation, $x$ in the general formula is 1.10, $3w$ is 1.85, and $ew = 4-2.65 = 1.35$, so that $e = 2.19$. The value of $f$ can be obtained by noting that $F/Si = f/(8-x) = 0.131$. Since $x$ equals 1.10, then $f = 0.90$. The coefficient, $d$, of the amount of exchange ion ($NH_4$) is 1.45. Therefore, the average formula for this example is

$$[(Al_{2.65} Ni_{1.85})^{VI} (Si_{6.90} Al_{1.10})^{IV} O_{20} (OH)_{3.1} F_{0.9}]$$
$$1.45 NH_4$$

Comparison of the defined ranges of $x$, $e$, $w$, $f$, and $d$ and the ions which can fill the roles of Y, Q and C with the results shown above demonstrates that the example falls within the scope of the defined formula.

An alternate method of calculation is based on the use of ionic ratios. However, the method is still dependent on the alumimum distribution between 4- and 6-fold states.

Let:
$R_1 = Si/Al = (8-x)/(4-ew) + x$
$R_2 = Si/Ni = (8-x)/3w$
$R_3 = Al^{IV}/Al^{VI}$
and
$R_4 = F/Si = f/(8-x)$.

Then it can be shown that:

$$x = (R_3/R_1 R_3 + R_1 + R_3 \quad (1)$$

$$w = (8-x)/3R_2 \quad (2)$$

$$e = (4R_3 - x)/w R_3 \quad (3)$$

and $$d \text{ (if exchange cation is monovalent)} = x + (e-2)3w \quad (4)$$

Once $x$ is obtained from the ratios and equation (1), $w$ can be calculated according to equation (2); $e$ from equation (3) with $x$ and $w$; and finally $d$ from equation (4). From the analysis given, $R_1 = 1.84$; $R_2 = 3.73$; and $R_4 = 0.131$. From the distribution given, $R_3 = 0.416$. Thus, $x = 1.10$; $w = 0.617$; $e = 2.19$; and $d = 1.45$ from equations (1) through (4), in good agreement with the values obtained by the distribution procedure. The value of $f$ can be recovered from $R_4$ as shown above. This calculation is presented simply to show the validity of equations (1) through (4). Given such validity, any analytical method or combination of methods that provides accurate values of the required ratios will give the correct values of $x$, $w$, $e$, and $d$.

As noted above, the heat activated minerals are suitable as catalysts for the conversion of hydrocarbon charge stocks in the presence of hydrogen. By a "hydrocarbon conversion process" is meant a conversion of hydrocarbons in the presence of hydrogen to some configuration different from the configuration of the starting hydrocarbons. Such change of configuration may be the result of isomerization (e.g., straight-chain paraffins to branch chain paraffins); dehydrogenation (e.g., naphthenes to aromatics); saturation (olefins to paraffins); hydrocracking (higher boiling hydrocarbons to lower boiling hydrocarbons); desulfurization; dehydrocyclization; and reforming. A hydrocarbon conversion process may be either hydrogen consuming or hydrogen producing. The addition and use of hydrogenating components to the heat activated minerals is also contemplated, and it will be obvious to those having ordinary skill in the art which hydrogenation components to distend upon the heat treated minerals in light of the particular reaction of interest. Similarly, those having ordinary skill in the art will understand the range of operating conditions at which the reaction of interest should be conducted since hydrocarbon coversion process, per se, as defined above are well known in the art.

The invention will be further described with reference to the following experimental work.

Hydroisomerization

The catalysts of this invention are particularly useful for the hydroisomerization of aliphatic hydrocarbons having from 4 to 10 carbon atoms per molecule under hydroisomerization conditions. The catalysts for isomerization are preferably prereduced with hydrogen but reduction of the catalysts can, of course, occur in situ. The catalysts have also been found to tolerate small concentrations of aromatics, olefins, sulfur and water normally present in feeds as natural gasoline.

Suitable hydroisomerization conditions include a temperature from 300° to 750° F., preferably 425° to 600° F.; a pressure of 100 to 10,000 psig, preferably 200 to 2000 psig; a liquid hourly space velocity (LHSV) based on the hydrocarbon charge of 0.10 to 10 volumes of hydrocarbon charges per volume of catalyst per hour, preferably from 0.5 to 4.0 v/v/hour; and a hydrogen to hydrocarbon mole ratio of from 0.5:1 to 20:1, preferably from 2:1 to 5:1.

The hydroisomerization aspect of this invention will be further described with reference to the following experimental examples.

EXAMPLE 6

The catalyst as prepared in Example 1 (1.4 weight percent nickel substitution) was calcined in air at 1000° F. for 10 hours and then reduced in hydrogen at 650° F. for 16 hours. This catalyst was then used as the catalyst for the isomerization of normal hexane by passage of the normal hexane downflow through a bed of the catalyst at 550° F.; 1.5 LHSV; 2.5 $H_2$:n-hexane; and a total pressure of 450 psig. The hexane conversion was 15 percent, with a 100 percent selectively to $C_6$ isomers. The results of this run are summarized in Table V below.

EXAMPLE 7

Example 6 was repeated except the catalyst employed was the same as that prepared in Example 1 above except sufficient additional nickel salt was employed to result in 2.4 weight percent nickel substitution. The percent hexane conversion was 30, with a 99 percent selectivity to $C_6$ isomers. This Example is also summarized in Table V below.

EXAMPLE 8

Example 6 was repeated except the catalyst was the same as that shown in Example 2 above (10.1% nickel substitution). The percent hexane conversion was 78, with 97 percent selectivity to $C_6$ isomers. This Example is also summarized in Tabel V below.

EXAMPLE 9

Example 8 repeated except the reaction temperature was reduced to 500° F. and the liquid hourly space velocity was reduced to 0.5. The percent hexane conversion was 68, while the percent selectivity to $C_6$ isomers was 98. The results of this Example are summarized in Table V below.

EXAMPLE 10

Example 9 was repeated except the reaction temperature was 450° F. and the percent hexane conversion was 27, while the percent selectivity to $C_6$ isomers was 100. The results of this Example are summarized in Table V below.

EXAMPLE 11

Example 6 was repeated except the catalyst contained no nickel substitution in the lattice and was prepared in accordance with the teachings of U.S. Pat. No. 3,252,757. The catalyst was calcined and reduced prior to use under the same conditions as the catalyst for Example 6 above. The percent hexane conversion was 12, with 100 percent selectivity to $C_6$ isomers.

This Example is also summarized in Table V below.

EXAMPLE 12

Example 6 was repeated except the catalyst consisted of 0.7% palladium and 15% nickel deposited by conventional impregnation techniques onto the catalyst of Example 11. The percent hexane conversion was only one, with 100 percent selectivity to $C_6$ isomers. This example is also summarized in Table V below.

EXAMPLE 13

Example 10 was repeated except the catalyst consisted of 1 percent palladium deposited on a mordenite base in the hydrogen form. This catalyst was prepared by impregnating a commercially obtained hydrogen mordenite (purchased from the Norton Company) with a solution of $Pd(NH_3)_4(NO_3)_2$ containing enough palladium salt to give 1.0 percent palladium on the finished catalyst. The percent hexane conversion was 7 with a percent selectivity to $C_6$ isomers of 100. The results are summarized in Table V below.

EXAMPLE 14

Example 13 was repeated except the reaction temperature was increased to 500° F. The percent hexane conversion was 24, with a percent selectivity to $C_6$ isomers of 100. This Example is summarized in Table V below.

EXAMPLE 15

Example 13 was repeated except the reaction temperature was 550° F. and the liquid hourly space velocity was 1.5. The percent hexane conversion was 31, and the percent selectivity to $C_6$ isomers was 98. The results of this run are summarized in Table V below.

EXAMPLE 16

Example 6 was repeated except the catalyst employed was the same as the catalyst prepared in Example 3 above (9.6% Ni from nickel acetate). The percent hexane conversion was 50, while the percent selectivity to $C_6$ isomers was 98. The results of this run are summarized in Table V below.

EXAMPLE 17

Example 16 was repeated except the catalyst of Example 16 was treated with HF to deposit 2 percent fluorine on the catalyst. The percent hexane conversion was 16, and the percent selectivity to $C_6$ isomers was 99. The results of this run are summarized in Table V below.

Referring to Table V below, a comparison of the Examples illustrates the advantage of including nickel in the lattice of the catalyst in accordance with the teachings of this invention.

TABLE V

Hydroisomerization of N-Hexane at 450 psig

| Ex. No. | Catalyst | Reaction Conditions Temp. ° F. | LHSV | $H_2$: Hexane | Conversion[a] | Weight % Hexane Selectivity[b] to $C_6$ Isomers |
|---|---|---|---|---|---|---|
| 6 | 0.7% Pd-1.4% Ni[c] | 550 | 1.5 | 2.5 | 15 | 100 |
| 7 | 0.7% pd-2.4% Ni | 550 | 1.5 | 2.5 | 30 | 99 |
| 8 | 0.7%Pd-10% Ni | 550 | 1.5 | 2.5 | 78 | 97 |
| 9 | 0.7% pd-10% Ni | 500 | 0.5 | 2.5 | 68 | 98 |
| 10 | 0.7% Pd-10% Ni | 450 | 0.5 | 2.5 | 27 | 100 |
| 11 | 0.7% Pd-0% Ni[d] | 550 | 1.5 | 2.5 | 12 | 100 |
| 12 | 0.7% Pd-15% Ni[e] | 550 | 1.5 | 2.5 | 1 | 100 |
| 13 | 1% Pd-H-mordenite | 450 | 0.5 | 2.5 | 7 | 100 |
| 14 | 1% Pd-H-mordenite | 500 | 0.5 | 2.5 | 24 | 100 |
| 15 | 1% pd-H-mordenite | 550 | 1.5 | 2.5 | 31 | 100 |
| 16 | 0.5% Pd-10% Ni[f] | 550 | 1.5 | 2.5 | 50 | 98 |
| 17 | 0.5% Pd-10% Ni | 550 | 1.5 | 2.5 | 16 | 99 |

[a]Conversion calculated by weight of hexane recovered divided by the weight of hexane charged.
[b]Selectivity calculated by weight of $C_6$ isomers produced divided by the weight of $C_6$ isomers which theoretically could have been produced.
[c]Catalysts for Examples 6 through 10 prepared using $NiF_2 \cdot 4H_2O$.
[d]Base synthetic mica montmorillonite (SMM) prepared in accordance with teachings of U.S. Pat. No. 3,252,757.
[e]Catalyst for Example 12 prepared by impregnating Pd and Ni onto the base SMM containing 0% Ni (catalyst for Ex. 11).
[f]Catalyst for Examples 16 and 17 prepared using Ni acetate The use of minor amounts of nickel in the lattice, for example, less than one percent, apparently has little effect on the activity of the catalyst for hexane hydroisomerization. This can only be seen by comparison of Examples 6 and 11 where the use of 1.4 percent nickel in the lattice (Ex. 6) resulted in only a three percent hexane conversion advantage over the same catalyst without nickel substitution in the lattice (Ex. 11). The percent hexane conversion decreases with decreasing reaction temperature as expected (Exs. 8–10). The catalysts of this invention have about a 50° F. temperature advantage over palladium on H-mordenite catalysts which are known for hexane hydroisomerization.

Referring to Table V above, a comparison of the Examples shows that for hexane hydroisomerization, the use of $NiF_2$ in the preparation of the nickel-substituted catalyst results in a more active catalyst than the catalyst prepared using nickel acetate as the salt. It should be noted, however, that the nickel-substituted catalysts of this invention, even when made from the nickel acetate salts, are still more active than the palladium-H-mordenite catalyst (Ex. 16 compared with Ex. 15). The addition of fluorine to the catalyst prepared using nickel acetate appears to decrease the activity of the catalyst for hexane conversion under the conditions shown in Example 17.

A further series of runs was made to study n-hexane hydroisomerization. In this series, the catalysts were prepared in a manner similar to the catalyst preparation in Example 4 above, i.e. using the nickel acetate salt. Varying amounts of nickel were substituted in the lattice structure by varying the amount of nickel acetate employed. The catalysts were calcined at 1000° F. for 10 hours and then reduced in hydrogen at 650° F. for 16 hours. The n-hexane was passed downflow through a bed of the catalyst at 500° F., 450 psig, a 1.0 liquid hourly space velocity based on the n-hexane, and an $H_2$/n-hexane mole ratio of 2.5. The results are shown in Table VI below:

ciency to the production of isomers. The selectivity to cracked products increased from 4 to 26 percent. Example B' shows the importance of using palladium along with lattice substituted nickel for excellent isomerization activity. To get good isomerization, both a dehydrogenation function and an acid function are required. The nickel-clay provides the acid function, and the impregnated Pd the dehydrogenation function.

Example C' in Table VI used a catalyst consisting of 1% palladium deposited on a commercially available H-mordenite zeolite. This is one of the better catalysts available today for isomerization as noted by the 98% selectivity to $C_6$ isomers. The conversion, however, is relatively low as is the weight percent 2,2-DMB in the product.

A further run was made to study the hydroisomerization of a $C_5$–$C_6$ fraction of natural gasoline.

TABLE VI

| Ex. No. | Catalyst[a] Wt % Ni | Substituted Nickel Atoms Per Unit Cell | Hexane Conversion Wt % | Selectivity WT % | | 2,2 DMB/$C_6$ Wt % |
|---|---|---|---|---|---|---|
| | | | | Isomerization to $C_6$ Isomers | Cracking | |
| 18 | 0 | 0 | 3.5 | 100 | — | <0.1 |
| 19 | 6.8 | 1 | 45 | 99 | — | 0.8 |
| 20 | 14.3[b] | 2 | 71 | 94 | 6 | 4.1 |
| 21 | 15 | 2 | 76 | 96 | 4 | 8.7 |
| 22 | 15 | 2 | 74 | 95 | 5 | 6.4 |
| 23 | 21.6 | 3 | 80 | 95 | 5 | 13.4 |
| 24 | 26.4 | 4 | 84 | 79 | 21 | 14.4 |
| 25 | 30.5 | 5 | 86 | 73 | 27 | 19.9 |
| 26 | 35.7 | 6 | 85 | 76 | 24 | 18.8 |
| A' | 15[c] | 0 | 0.9 | 100 | — | <0.1 |
| B' | 15[d] | 2 | 26 | 74 | 26 | 0.4 |
| C' | 0[e] | 0 | 33 | 98 | 2 | 3.5 |

[a]All catalysts except Example B' contain from 0.5% to 0.7% Pd.
[b]This catalyst contained 0.61% fluoride compared to 1.01% for the catalyst for Example 21.
[c]Catalyst of Example 12.
[d]Catalyst 21 without palladium.
[e]Catalyst of Example 13.

Referring to Table VI, it can be seen that the hexane conversion generally increases with increased nickel in the lattice up to about 30% nickel. Similarly, the weight percent 2,2-dimethylbutane ("2,2-DMB") in the product having six carbon atoms increased with increasing nickel in the lattice to about 30% nickel. The weight percent 2,2-DMB was calculated by dividing the weight of 2,2-DMB in the product by the total weight of hydrocarbons in the product having six carbon atoms. The conversion of hexane to one-branched isomers occurs readily compared to the difficulty in the production of the double branched 2,2-DMB. Thus, as the percent nickel increases to about 30%, the catalysts are showing much more acidity, for the production of 2,2-DMB is really a measure of the surface acidity. The nickel is thus not functioning as surface deposited nickel but is part of the structure and lends itself to increasing the surface acidity and thus to increasing the isomerization activity of the catalyst. In Example A' on Table VI above, the catalyst of Example 12 was used (base synthetic mica montmorillonite having 0.7% Pd and 15% nickel deposited thereon by convertional impregnation techniques) and the conversion was less than 1 percent. This result should be contrasted with the results in Examples 20 and 21 where about 15% nickel was substituted in the lattice and conversions of about 75% were achieved with as much as 8.7 percent 2,2-DMB in the product.

Example B' in Table VI illustrates the importance of a hydrogenation component on the base catalysts of this invention. Example B' uses the same catalyst as in Example 21 except Pd is not deposited on the catalyst, and the conversion of hexane drops as well as the efficiency to the production of isomers.

EXAMPLE 27

In the run for this Example, a $C_5$–$C_6$ fraction of natural gasoline, whose properties are shown in Table VII below, was passed downflow through a bed of a catalyst the same as that employed in Example 25 above. The reaction conditions included a temperature of 450° F., psig, a 0.5 liquid hourly space velocity, and a hydrogen to hydrocarbon ratio of 2.5. The properties of the product are also shown on Table VII below.

TABLE VII

Hydroisomerization of $C_5$/$C_6$ Fraction of Natural Gasoline

Catalyst: 0.7% Pd on 30.5% Ni SMM
Conditions: 450° F., 0.5 LHSV, 2.5 $H_2$/HC, 450 psig

| Component | Feed (wt%) | Product (wt%) |
|---|---|---|
| $C_1$ – $C_4$ | | 3.6 |
| isopentane | 12.1 | 30.7 |
| n-pentane | 35.0 | 15.1 |
| 2,2-dimethylbutane | 1.9 | 8.1 |
| 2,3-dimethylbutane | 3.3 | 3.9 |
| 2-methylpentane | 16.0 | 16.6 |
| 3-methylpentane | 11.8 | 11.8 |
| n-hexane | 19.9 | 9.3 |
| Estimated RON clear of $C_5$/$C_6$ fraction | 63 | 76 |

Referring to Table VII it can be seen that the $C_5$ and $C_6$ components of the product are close to their equilibrium concentrations.

Hydrocracking

The catalysts of this invention are also useful for the hydrocracking of hydrocarbons to produce lighter boiling materials than the original charge stock. For example, the catalysts of this invention are useful for the hydrocracking of aliphatic hydrocarbons to produce lighter boiling materials such as the cracking of raffinates to produce liquid petroleum gas. The catalysts are also useful for the hydrocracking of higher boiling mixtures of hydrocarbons such as those boiling from 450°0 F. to 950° F. at atmospheric pressure, especially furnace oils, to produce gasoline range hydrocarbons of high octane number. One of the unique features of the catalysts of this invention is that during the hydrocracking of a furnace oil, the aromatic content of the furnace oil is retained. The ability of the layered clay-type base to retain or preserve the aromatic content of furnace oils on hydrocracking appears to be due to the presence of nickel substituted in the lattice. The catalysts of this invention are also suitable for the hydrocracking of higher boiling stocks such as gas oils or heavier to produce lighter boiling hydrocarbons.

Suitable hydrocracking conditions include a temperature from 350° F. to 1000° F., preferably 500° F.; a pressure from 250 to 10,000 psig, preferably from 400 to 3000 psig; a liquid hourly space velocity based on the hydrocarbon charge of 0.1 to 10 volumes of hydrocarbon charge per volume of catalyst per hour, preferably from 0.25 to 5 v/v/hour; and a hydrogen to hydrocarbon mole ratio of from 0.5:1 to 20:1, preferably from 2:1 to 10:1. The optimum hydrocracking conditions, while generally falling within the above ranges, may be varied depending on the particular charge stock employed. In general, the higher hydrocracking temperatures will be employed with the heavier hydrocarbon charge stocks.

It has also been found that the catalysts of this invention are improved in their hydrocracking ability by a sulfiding treatment. The sulfiding can be done by any method which is well recognized in the art, such as by the pre-addition of $H_2S$ in a hydrogen carrier gas to the catalyst for suitable periods of time such as 1 to 24 hours at suitable temperatures such as 500° F. to 950° F. Sulfiding can also be done during the startup procedure by adding sulfur compounds to the charge stock and sulfur can thereafter be added continuously during the run. Suitable sulfur compounds would include $H_2S$ and carbon disulfide.

The hydrocracking aspect of this invention will be further described with reference to the following experimental work.

Normal Hexane Hydrocracking

A series of catalysts were prepared as in Example 4 using nickel acetate (Ni(Ac)$_2$) as the nickel salt and varing the amount of nickel substituted in the lattice. Each of the catalysts was treated to contain approximately 0.5% to 0.7% Pd. The dried catalysts were calcined in air at 1000° F. for 10 hours and then treated with a mixture of 98 percent $H_2$ and 2% $H_2S$ at 750 F. for 16 hours to sulfide. Normal hexane was passed downflow through a bed of the catalyst at 650° F., 1.5 liquid hourly space velocity based on the n-hexane, 450 psig, and an $H_2$/n-hexane mole ratio of 2.5. The results of the series of runs are shown in Table VIII below:

TABLE VIII

Hydrocracking of N-Hexane
Conditions: 1.5 LHSV; 450 psig; 2.5 $H_2/C_6$

| Example No. | Catalyst Wt % Ni | Temperature ° F. | Weight % n-Hexane Converted to Cracked Product[a] |
|---|---|---|---|
| 28 | 0[b] | 650 | 2 |
| 29 | 1.4[c] | 650 | 6 |
| 30 | 6.8 | 650 | 28 |
| 31 | 9.7 | 650 | 39 |
| 32 | 10.1[d] | 650 | 68 |
| 33 | 14.3 | 650 | 69 |
| 34 | 21.6 | 650 | 100 |
| 35 | 21.6 | 600 | 66 |
| 36 | 26.4 | 600 | 62 |
| 37 | 30.5 | 600 | 100 |
| 38 | 35.7 | 600 | 100 |
| 39 | 30.5 | 550 | 69 |
| 40 | 35.7 | 550 | 46 |

[a]Calculated by dividing weight of cracked products recovered by the weight of n-hexane charged.
[b]Same as catalyst for Ex. 11 except calcined and presulfided as set forth above.
[c]Same as catalyst for Ex. 1 and then calcined and presulfided as set forth above.
[d]NiF$_2$ was salt employed in preparing this catalyst.

EXAMPLE 41

Example 28 was repeated except the catalyst employed was a commercially available rare-earth exchanged form Linde-type Y molecular sieve containing 0.5 weight percent palladium. The weight percent hexane converted to cracked products was 7.2.

EXAMPLE 42

Example 41 was repeated except the reaction temperature was increased to 725° F., which resulted in an increase in hexane converted to cracked products to 50 weight percent.

Referring to Table VIII, it can be seen the substitution of nickel in the lattice of the layered synthetic mica/montmorillonite clay greatly improves the ability of the catalyst to crack normal hexane. It would appear that the catalysts of this invention have a temperature advantage over other commercial catalysts such as the palladium containing rare-earth exchanged Y-zeolites.

Table IX below shows the complete product distribution for the products from Examples 32, 41 and 42 given above.

Referring to Table IX it can be seen that the nickel-substituted catalysts of this invention have a great advantage over the catalyst used in Examples 41 and 42. The weight percent isobutane in the product, for example, in Example 32 was 8.7, versus only 1.4 weight percent using the Y-zeolite. For example, the catalyst of Example 12 was tested for the hydrocracking of n-hexane under the conditions of Example 32 above, and only 7 percent of the hexane was converted to cracked products compared to 68 percent for Example 32. This catalyst (15% Ni deposited on SMM) was approximately as active as the Pd-rare earth Y-zeolite of Example 41 but far less active than the catalyst containing about the same amount of nickel incorporated into the structure (Ex. 32).

TABLE IX

Product Analysis for n-Hexane Hydrocracking

| Example No. | 32 | 41 | 42 |
|---|---|---|---|
| Catalyst | 0.7% Pd- 10% Ni Sulfided | 0.5% Pd on rare earth-Y zeolite sulfided | 0.5% Pd on rare earth-Y zeolite sulfided |
| Reaction Conditions | | | |

TABLE IX-continued

Product Analysis for n-Hexane Hydrocracking

| Temperature | 650° F. | 650° F. | 725° F. |
|---|---|---|---|
| Pressure, psig | 450 | 450 | 450 |
| LHSV, v/v/hr | 1.5 | 1.5 | 1.5 |
| H$_2$:n-hexane | 2.5 | 2.5 | 2.5 |
| Product Distribution (wt % of product) | | | |
| C$_5$+ | 45.7 | 95.2 | 61.2 |
| i-C$_4$ | 8.7 | 1.4 | 6.0 |
| n-C$_4$ | 10.3 | 0.4 | 1.0 |
| C$_3$ | 33.8 | 3.0 | 30.0 |
| C$_2$ | 1.1 | — | 1.3 |
| C$_1$ | 0.4 | — | 0.5 |
| Total C$_5$ (wt %) | 14.0 | 2.7 | 11.7 |
| Total C$_6$ (wt %) | 31.8 | 92.5 | 49.5 |
| Hexane Converted to Cracked Products (w %) | 68.2 | 7.5 | 50.5 |
| C$_6$ Distribution (wt %) | | | |
| 2,2-dimethylbutane | 11 | 4 | 18 |
| 2,3-dimethylbutane + 2-methylpentane | 47 | 42 | 36 |
| 3-methylpentane | 13 | 23 | 21 |
| n-hexane | 29 | 31 | 26 |

EXAMPLE 43

Example 32 was repeated except the catalyst was prepared using nickel acetate as the salt rather than nickel fluoride. The percent hexane conversion was 80, while the percent selectivity to C$_6$ isomers and cracked products was 50 and 50, respectively. The results of this run are also summarized in Table X below.

EXAMPLE 44

Example 43 was repeated except the catalyst additionally contained 2 percent fluorine, which was added by the use of HF. The percent hexane conversion was 98, while the percent selectivity to C$_6$ isomers and cracked products was 27 and 73 percent, respectively. This run is also summarized in Table X below.

EXAMPLE 45

Example 32 was repeated except the catalyst was the same as that used in Example 41. The percent hexane conversion was 72, while the percent selectivity to C$_6$ isomers and cracking was 90 and 10 percent, respectively. The results of this run are also summarized in Table X below.

TABLE X

Hydrocracking$^a$ of n-Hexane

| Ex. No. | Catalyst | Wt % n-Hexane Converted$^b$ | Wt % Selectivity$^c$ to | |
|---|---|---|---|---|
| | | | C$_6$ Isomers | Cracked Products |
| 32 | 0.7% Pd-10% Ni$^d$ | 91 | 25 | 75 |
| 43 | 0.7% Pd-10% Ni$^e$ | 80 | 50 | 50 |
| 44 | 0.7% Pd-10% Ni$^e$ plus 2% F by HF | 89 | 27 | 73 |
| 45 | 0.5% Pd-rare earth-Y-Zeolite | 72 | 90 | 10 |

$^a$Hydrocracking conditions: 650° F.; 450 psig; 1.5 LHSV; and 2.5 H$_2$:n-hexane.
$^b$Conversion calculated by weight of n-hexane recovered divided by weight of n-hexane charged.
$^c$Selectivity calculated by the weight of products recovered divided by the weight of converted hexane.
$^d$NiF$_2$ used as nickel salt.
$^e$Ni(Ac)$_2$ (nickel acetate) used as nickel salt.

Referring to Table X, a comparison of the Examples from this Table and those in Table VIII shows that the nickel-substituted catalyst made from nickel fluoride is more active than the catalyst made from nickel acetate. However, the nickel-substituted catalyst using nickel acetate is still more active than the Y-zeolite catalyst. Also, for hydrocracking, the addition of fluorine using HF promotes the activity of the nickel-substituted catalyst made from nickel acetate to about the same level as the nickel-substituted catalyst which is prepared using nickel fluoride. This result was unexpected in view of the fact that the addition of fluorine did not appear to increase the activity of the catalyst for the isomerization of normal hexane.

EXAMPLE 46

Example 44 was repeated except using a Co substituted catalyst instead of the nickel substituted catalyst of Example 44, The final catalyst contained about 0.7% Pd and about 7% Co. The catalyst was prepared in a manner similar to Example 5 above and presulfided for 16 hours at 750° F. using a mixture of 98% H$_2$ and 2% H$_2$S. The weight percent hexane converted to cracked products was 5%.

FURNACE OIL HYDROCRACKING

The purpose of the hydrocracking of furnace oil is, in most cases, to produce a gasoline having as high an octane rating as possible. In some instances, the main purpose is to produce gaseous olefins such as ethylene and propylene. In all instances, the product has a lower boiling range than the charge stock. The nickel-substituted synthetic mica/montmorillonite catalysts of this invention, especially those containing a hydrogenation component, can suitably be employed in a hydrocracking operation at conventional conditions. Generally, and preferably, for hydrocracking, a metal or metals having hydrogenation activity from Groups VI and VIII are incorporated into the nickel-substituted materials of this invention. Any of the metals having hydrogenation activity as noted above can be employed with the preferred metals being the noble metals, and especially palladium.

The amount of metals to deposit can be within the ranges set forth above in the discussion of the catalyst preparation techniques. The method of adding the metals can also be as set forth above. The catalyst can be dried and calcined as noted above and is preferably presulfided such as by pretreatment at 600° F. and atmospheric pressure using a mixture of 8% H$_2$S and 92% hydrogen prior to the furnace oil hydrocracking runs.

Suitable conditions for the hydrocracking of furnace oils are set forth generally above under n-hexane hydrocracking. The preferred conditions for the hydrocracking of furnace oils include 500–1500 psig, 0.5–5 LHSV, 5000 – 15,000 SCF H$_2$/bbl., and 450°–850° F.

While the process of the present invention can be practiced using a furnace oil containing relatively large amounts of nitrogen-containing compounds, it is preferred to reduce the nitrogen level of the charge to a reasonably low level by prior hydrotreatment before hydrocracking using the catalysts of this invention or other suitable hydrogenation catalysts. For example, it is preferred that the organic nitrogen level be less than 10 parts per million (ppm), more preferably less than 1 ppm.

FIG. 2 is a flow diagram of a preferred scheme for the hydrocracking of a furnace oil to produce a high quality naphtha.

Referring to FIG. 2, the raw furnace oil enters through line 10 where it is admixed with fresh hydrogen from line 12 and recycle hydrogen from line 14 and the admixture is passed downflow through the first reaction zone 16 where it contacts a hydrogenation catalyst under conditions applicable for the desulfurization and denitrogenation of the furnace oil with little hydrocracking. The catalyst can be any of the well known hydrogenation catalysts such as one or more of the supported Group VI or iron group metals, metal oxides or metal sulfides on a high area support, such as an alumina. The catalysts of this invention may also be employed. The reaction conditions usually include a total pressure of 500 to 10,000 psig, preferably 1500 to 3000 psig, and wherein the partial pressure of hydrogen is 300 to 8000 psig, preferably 1200 to 2500 psig. The temperature can suitably be from 400° to 1000° F., preferably between 500° to 800° F., and the liquid hourly space velocity can be from 0.1 to 20, preferably from 0.25 to 4 volumes of liquid charge per volume of catalyst per hour. From 1500 to 10,000, usually 3000 to 7000 ft$^3$ of hydrogen are employed per barrel of oil, the flow of hydrogen being the sum of the fresh hydrogen (line 12); the recycle hydrogen (line 14) and the quench hydrogen (lines 18 and 20).

The pretreated furnace oil exits from reactor 16 through line 22 where it enters gas separator 24. The function of separator 24 is to remove recycle hydrogen through line 26 for return to reactor 16 through lines 14, 18 and 20. The function of the recycle hydrogen entering through lines 18 and 20 is as a quench to control the temperature in the reactor 16.

The remaining products exit from separator 24 through line 28 and enter distillation zone 30 where fuel gas is removed overhead through line 32. The liquid pretreated furnace oil exits from distillation zone 30 through line 34 where it is combined with recycle oil from line 74; fresh hydrogen from line 36; and recycle hydrogen from line 38. The combined stream passes downflow through reactor 40 containing a bed of the catalyst of this invention. The reaction conditions include a total pressure of 150 to 10,000 psig, with a hydrogen partial pressure of 100 to 8000 psig. The preferred total pressure is 500 to 3000 psig with the preferred partial pressure of hydrogen as 300 to 2500 psig. The temperature can be 400° to 1000° F.; preferably 500° to 800° F. The liquid hourly space velocity can suitably be from 0.1 to 20, preferably 0.5 to 5 volumes of liquid charge per volume of catalyst per hour. Quench hydrogen may enter reactor 40 through lines 42 and 44. The products exit through line 46 and enter separator 48 where recycle hydrogen is removed through line 50 and enters reactor 40 through lines 38, 42 and 44. The remaining products exit separator 48 through line 52 and are sent for separation. For example, the products may enter a distillation zone 54 where $C_4$ and lighter products are removed overhead through line 56 and are further separated in a distillation zone 58 by removal of fuel gas through line 60; $C_5$ hydrocarbons through line 62; and $C_4$ hydrocarbons through line 64. The bottoms from zone 54 are removed through line 66 and enter distillation zone 68 for removal of light gasoline through line 70; naphtha through 72 and recycle oil through line 74.

The furnace oil hydrocracking aspect of this invention will be further described with reference to the following experimental work.

EXAMPLE 47

In the run for this Example, the catalyst was prepared as in Example 1. The catalyst was calcined at 1000° F. for 16 hours and was then sulfided at 600° F. with a mixture of 8% $H_2S$ and 92% $H_2$ for one hour. An FCC furnace oil whose characteristics are given in Table XI below (GR 63903) was passed downflow through a bed of the above catalyst at 700° F., 1500 psig, liquid hourly space velocity of 1, together with hydrogen at a rate of 10,000 standard cubic feet per barrel. The volume percent yield of lighter than 400° F. naphtha was 43% by volume. The aromatics content of the total liquid product was 39 volume percent. Analysis of the liquid products obtained are summarized in Table XII.

TABLE XI

|  | FCC Furnace Oil GR 63903 | Pretreated FCC Furnace Oil GR 74103 |
|---|---|---|
| Gravity (ASTM D287-67) ° API | 23.1 | 28.6 |
| Sulfur (wt %) | 0.88 | 0.0066 |
| Nitrogen (ppm) | 336 | 1.0 |
| Carbon Residue, Rams (ASTM D524) wt% | 0.10 | — |
| Hydrocarbon Type Analysis FIA (ASTM D1319-70) |  |  |
| Aromatics (vol %) | 61 | 58.3 |
| Olefins (vol %) | 7 | 2 |
| Saturates (vol %) | 32 | 40 |
| Distillation (ASTM D86-76) |  |  |
| Overpoint ° F. | 386 | 297 |
| Endpoint ° F. | 650 | 621 |
| 10%: Volume % | 462 | 440 |
| 30% | 496 | 470 |
| 50% | 524 | 496 |
| 70% | 558 | 525 |
| 90% | 604 | 570 |

EXAMPLE 48

Example 47 was repeated except using the catalyst of Example 11 (0.7% Pd on SMM) except the catalyst pretreatment was the same as in Example 47. The yield of lighter than 400° F. naphtha was 56. The results of this run are summarized in Table XII.

TABLE XII

| Hydrocracking of FCC Furnace Oil (GR 63903) (1500 psig; 700° F.; 1 LVHSV; 10,000 SCF $H_2$/Bbl) | | |
|---|---|---|
|  | Ex. 47 0.7% Pd-Ni (1.4%) SMM | Ex. 48 0.7% Pd-SMM |
| On-Stream Time, Hrs. | 4–36 | 4–36 |
| Gravity ° API | 43 | 47.4 |
| Sulfur (wt %) | 0.05 | 0.04 |
| Nitrogen (ppm) | 0.4 | 3 |
| Hydrocarbon Type Analysis FIA |  |  |
| Aromatics (vol. %) | 39 | 14 |
| Olefins (vol. %) | 2 | 1 |
| Saturates (vol. %) | 59 | 85 |
| Liquid Recovery (vol. %) | 107.3 | 98 |
| <400° F. Naphtha (vol. %) in Liquid Product | 40 | 57 |
| Vol. % Yield of <400° F. Naphtha[1] | 43 | 56 |
| Vol. % Yield of Aromatics[2] | 42 | 14 |

[1] Volume % yield of <400° F. naphtha is calculated by multiplying Liquid Recovery (%) by Vol. fraction of <400° F. naphtha.
[2] Volume % Aromatics is obtained by multiplying Liquid Recovery (%) by Vol. fraction of aromatics.

EXAMPLE 49

The catalyst prepared and pretreated in the same manner as in Example 2 above using the pretreatment of Example 47 above was employed.

A pretreated FCC furnace oil (GR 74103) whose characteristics are given in Table XI above was passed downflow through a bed of the above catalyst at 1500 psig, together with hydrogen at at rate of 10,000 SCF/bbl., 650° F., and an LHSV of 2. Table XIII shows the hydrocracking activity of this catalyst after being lined out.

TABLE XIII

Hydrocracking of FCC Furnace Oil and Pretreated FCC Furnace Oil (1500 psig; 650° F.; 10,000 SCF $H_2$/bbl) with the 0.7% pd - 10.1% Ni SMM)

|  | Ex. 49 Pretreated FCC Furnace Oil (GR 74103) 2 LHSV | Ex. 50 Furnace Oil (GR 63903) 1 LHSV |
|---|---|---|
| On-Stream Time, Hrs. | 14 | 16 |
| Gravity ° API | 81.1 | 28.9 |
| Sulfur (wt %) | 0.04 | 0.31 |
| Nitrogen (ppm) | 0.6 | 20.6 |
| Hydrocarbon Type Analysis FIA | | |
| Aromatics (vol. %) | 2 | 65 |
| Olefins (vol. %) | 0.5 | 1 |
| Saturates (vol. %) | 97.5 | 34 |
| Liquid Recovery (vol. %) | 52.2 | 96.2 |
| <400° F. Naphtha (vol. %) in Liquid Product | 100 | 14 |
| Volume Yield of <400° F. Naphtha$^a$ | 52.2 | 13.47 |
| Volume Yield of Aromatics$^b$ | 1.04 | 62.5 |

$^a$Calculated by multiplying liquid recovery (%) by volume fraction of <400° F. naphtha.
$^b$Calculated by multiplying liquid recovery (%) by volume fraction of aromatics.

EXAMPLE 50

Example 49 was repeated except the charge stock was the FCC furnace oil (GR 69303) shown in Table XI; the LHSV was 1 and the catalyst was the same as that used in Example 49 after about 124 hours of operation. The results of the run are also summarized in Table XIII above.

Referring to Table XIII, the presence of nitrogen in the feed to Example 50 is primarily responsible for the decreased hydrocracking activity of the catalyst as shown by the decreased "<400° F. Naphtha (Vol. %) in Liquid Product" and decreased "Volume Yield of <400° F. Naphtha".

Comparison runs were made to show the effect of the catalysts of this invention on the retention of aromatics using low nitrogen content furnace oils. The low nitrogen content furnace oils were obtained by hydrogen pretreatment of FCC furnace oils.

EXAMPLE 51

A pretreated FCC oil whose characteristics are given in Table XI above was passed downflow through a bed of the same catalyst used in Example 49 at 1500 psig, together with hydrogen at 10,000 SCF $H_2$/bbl., 2 LHSV, and a temperature of 600° F. The liquid recovery was 81.1 volume percent, the volume yield of of <400° F. naphtha was 81.1%, and the volume of aromatics was 11.0%. More detailed results appear in Table XIV.

EXAMPLE 52

A pretreated FCC furnace oil (GR 74103) whose characteristics are given in Table XI above was passed downflow through a bed of the same catalyst prepared as in Example 11 above except the pretreatment was the same as in Example 47. The reaction conditions included a pressure of 1500 psig; a hydrogen flow rate of 10,000 SCF $H_2$/bbl; a 2 LHSV; and a temperature of 500° F. The liquid recovery was 109 volume %, the volume yield of <400° F. naphtha was 81.8%, and the volume yield of aromatics was 1.1%. More detailed analyses of the product appear in Table XIV.

Comparable conversions were obtained in Examples 51 and 52 as shown by the similar gravities of the liquid products. As can be seen from Table XIV, the volume yield of aromatics in in the product using the catalyst of this invention (Ex. 51) is 11% versus only 1.1% when no nickel is substituted in the lattice (Ex. 52).

TABLE XIV

Hydrocracking of Pretreated FCC Furnace Oil
(1500 psig; 2 LVHSV; 10,000 SCF $H_2$/Bbl)

|  | Ex. 51 0.7% Pd-Ni (10.1%) SMM | Ex. 52 0.7% Pd-SMM |
|---|---|---|
| On-Stream Time, Hrs. | 8 | 24 |
| Temperature ° F. | 600 | 500 |
| Gravity ° API | 53.1 | 51.9 |
| Nitrogen (ppm) | 0.4 | <0.2 |
| Hydrocarbon Type Analysis FIA | | |
| Aromatics (vol %) | 11.0 | 1.0 |
| Olefins (vol %) | 1.0 | 0.0 |
| Saturates (vol %) | 88.0 | 99.0 |
| Liquid Recovery (vol %) | 81.1 | 109 |
| <400° F. Naphtha (vol %) in liquid product | 100 | 75 |
| Volume Yield of <400° F. Naphtha$^{(1)}$ | 81.1 | 81.8 |
| Volume Yield of Aromatics$^{(2)}$ | 8.9 | 1.1 |

$^{(1)}$Calculated by multiplying "Liquid Recovery (vol %) " by volume fraction of <400° F. naphtha.
$^2$Calculated by multiplying "Liquid Recovery (vol %)" by volume fraction of aromatics.

A pretreated FCC furnace oil whose characteristics are given in Table XI above was used in the following examples to determine the effect of the nickel substitution level on hydrocracking activity and selectivity. The pretreated FCC furnace oil (GF 74103) was contacted with various nickel substituted catalysts under the conditions set forth in Table XV below. The results of the runs are also set forth in Table XV below.

TABLE XV

Hydrocracking of Pretreated Furnace Oil
(1500 psig; 2 LVHSV; 10,000 SCF $H_2$/Bbl)

| Ex. No. | Catalyst$^a$ Wt % Ni | Temp. ° F. | Gravity ° API | Liquid Recovery % | Aromatics % | <400° F. Naphtha % |
|---|---|---|---|---|---|---|
| 53 | 0 | 500 | 51.9 | 95 | 1 | 75 |
| 54 | 1.4 | 550 | 56.6 | 88 | 13 | 80 |
| 55 | 10 | 600 | 53.3 | 90 | 17 | 90 |
| 56 | 30.5 | 565 | 50 | 60 | 25 | 95 |

$^a$Catalysts were same as those used in Examples 11, 6, 8 and 25 respectively, except the pretreatment was the same as Example 47.

Referring to Table XV, the aromatics retention increases with an increasing nickel content of the catalyst, although at 30.5% nickel (Ex. 56), the liquid recovery was down.

A series of runs was made the same as the run for Example 54, except the temperature was varied. The results are shown in Table XVI below.

TABLE XVI

| Example No. | Temp. °F. | Gravity of Liquid Product °API |
|---|---|---|
| 57 | 500 | 33 |
| 54 | 550 | 56.6 |
| 58 | 600 | 78 |
| 59 | 650 | 82 |

Similar results were obtained using the catalyst from Example 55.

Raffinate Hydrocracking

Raffinate for purposes of this application is defined as a predominantly paraffinic stream which remains after aromatics are extracted from a stream containing large amounts of aromatics, such as a reformer effluent. A raffinate having the characteristics shown in Table XVII below was subjected to hydrocracking. Usually a raffinate has a boiling range from 100° to 400° F. at atmospheric pressure (ASTM D-86-76).

TABLE XVII

| Component | Vol. % |
|---|---|
| Paraffins | 90.80 |
| $C_4$    0.15 | |
| $C_5$    2.44 | |
| $C_6$   71.34 | |
| $C_7$   16.68 | |
| $C_8^+$  0.19 | |
| Naphthenes | 7.11 |
| Aromatics | 2.08 |

The conditions of hydrocracking and the results are shown in Table XVIII below using a variety of nickel substituted catalysts.

TABLE XVIII

| Raffinate Hydrocracking | |
|---|---|
| Conditions of Run: | 1000 psig; 2.0 LHSV; 4 $H_2$/hydrocarbon. |
| Feed: | Raffinate of Table XVII plus 1500 ppm S added as $CS_2$ |

| Ex. No. | Catalyst[a] Wt % Ni | Temp. °F. | $C_3+C_4$ Vol. % | $C_5^+$ Vol. % | $C_1+C_2$ Wt % |
|---|---|---|---|---|---|
| 60 | 0 | 750 | 13.5 | 88.5 | 0.41 |
| 61 | 15 | 625 | 48.1 | 60.0 | 0.66 |
| 62 | 21.6 | 625 | 46.3 | 62.0 | 0.39 |
| 63 | 30.5 | 600 | 47.5 | 60.4 | 0.8 |

[a]Catalysts were the same as those used in Exs. 11, 21, 23 and 25, respectively, except the catalyst was pretreated for 16 hours at 750° F. with a stream of 2% $H_2S$ - 98% $H_2$.

The desired raffinate product is the volume percent $C_3+C_4$ which is defined here as LPG (liquid petroleum gas). The volume percent LPG is increased considerably at lower temperatures when using the nickel substituted catalysts of this invention. That the catalyst of Example 60 was low in activity at 750° F. is shown by the low yield of products having three and four carbon atoms.

The catalyst of this invention was also employed for residue desulfurization. The feedstock was a residue having the characteristics shown in Table XIX below.

TABLE XIX

| Properties | Charge Stock | Product Example 64 |
|---|---|---|
| Gravity: °API | 15.2 | 18.4 |
| Sulfur: wt % | 4.13 | 2.32 |
| $C_5$ Insolubles: | | |
| wt % | 6.34 | 4.42 |
| Nickel: ppm | 19 | 14 |
| Vanadium | 58 | 32 |

EXAMPLE 64

The charge stock shown in Table XIX above was passed down flow at 1000 psig; 700° F; 5000 SCF of $H_2$ per barrel of charge and a 1 liquid hourly space velocity through a bed of a catalyst consisting of 10% molybdenum deposited on a layered synthetic mica/montmorillonite containing 10 weight percent nickel proxying for the aluminum atoms in the octahedral sites. The 10% nickel substituted material was prepared in a manner similar to that described in Example 3 above except no Pd was added. The molybdenum was deposited from an aqueous solution of ammonium paramolybdate using the so-called incipient wetness or minimum excess solution technique. The properties of the product are summarized in Table XIX above.

Referring to Table XIX, it can be seen that almost half the sulfur was removed. In contrast, a catalyst consisting of 0.5% Ni, 1% Co and 8% molybdenum deposited on the layered synthetic mica/montmorillonite with 0% nickel substitution (the catalyst of Example 11) was substantially inactive for residue desulfurization, the product showing 3.9% sulfur.

EXAMPLE 65

26.0 g. of hydrated alumina, $Al_2O_3 \cdot 3H_2O$ (Alcoa C31, 64.9% $Al_2O_3$) were added with stirring to a polysilicic acid sol which was prepared by passing sodium silicate over a hydrogen resin. The volume of sol was chosen so as to contain 27.2 g. of $SiO_2$. 5.0 g. of Co-$(Ac)_2 \cdot 4H_2O$, 15.0 g. of $Ni(Ac)_2 \cdot 4H_2O$, 0.78 g of $NH_4F$, and 0.42 g. of HF were dissolved in 75 cc. of water and the solution was added, with stirring, to the silica-alumina slurry. The pH of the slurry was adjusted to 8.0 using aqueous ammonia. The final feed slurry was stirred for 30 minutes, charged to a stirred autoclave, heated quickly (1 to 1½ hrs.) until the pressure lined out at 1250 psig (300° C.) and maintained at these conditions for 4 hours. The product was cooled in the pressure vessel, removed, sheared in a blender to insure homogeneity, filtered and dried at about 250° F. Palladium was added to the dried product using conventional impregnation techniques. The final catalyst contained 2.5% Co, 7.5% Ni, and 0.5% Pd.

EXAMPLE 66

Example 28 was repeated except using the catalyst of Example 65 and the weight percent n-hexane converted to cracked products was 54%.

Resort may be had to such variations and modifications as fall within the spirit of the invention and the scope of the appended claims.

We claim:

1. A process for the conversion of hydrocarbons in the presence of hydrogen which comprises contacting a mixture of hydrogen and said hydrocarbons under hydrocarbon conversion conditions with a catalyst comprising:

a laminar 2:1 layer-lattice aluminosilicate mineral possessing layer-lattice unit cells, each cell having an inherent negative charge balanced by cations exterior to said unit cell, said mineral corresponding to the following overall formula prior to drying and calcining:

$$[(Al_{4-ew}^{3+} Y_{3w}^{2+})^{VI} (Q_{8-x}^{4+} Al_x^{3+})^{IV} O_{20}(OH)_{4-f} F_f] \cdot [dC^y]$$

where
Al is aluminum;
Y is selected from the class consisting of nickel, cobalt and mixtures thereof;
Q is at least 0.95 mol fraction silicon ions, the remainder consisting of tetravalent ions having an ionic radius not to exceed 0.65 A; and
F is fluorine;
C is at least one charge-balancing cation; and where e has a numerical value from 2 to 3 inclusive;
w has a numerical value from 0.01 to 2 inclusive, with the proviso that the quantity ew have a numerical value from 0.02 to 4 inclusive;
f has a value of 4 or less;
x has a numerical value from 0.05 to 2.0 inclusive;
y is the valence of the cation C;
d is the number of cations C where the product $dy = x + 3(e-2)w$;
and wherein said first bracket represents said layer-lattic unit cell formulation and said second bracket represents said charge-balancing cations.

2. A process according to claim 1 wherein said Y consists essentially of nickel.

3. A process according to claim 1 wherein Q is silicon.

4. A process in accordance with claim 3 wherein said second bracket has the composition:

$$[a M^n + b Al(OH)_{3-z}^z]$$

wherein $$an + bz = dy = x + 3(e-2)w$$

and M is a cation selected from the group consisting of hydrogen, ammonium, multivalent metal cations other than aluminum, and partial hydroxides of multivalent metal cations, and n is the unsatisfied valence of M.

5. A process in accordance with claim 3 wherein said C is selected from the group consisting of hydrogen, alkaline earth metal, heavy metal, heavy-metal partial hydroxides, ammonium, substituted ammonium, and substituted phosphonium cations and mixtures thereof.

6. A process in accordance with claim 5 wherein C is primarily hydrogen.

7. A process in accordance with claim 6 wherein e has a value of about 2; w has a value from 0.2 to 1.66; x has a value from 0.5 to 2; and the value of f is from 0.5 to 3.75.

8. A process in accordance with claim 7 wherein x is about 1.5.

9. A process in accordance with claim 8 wherein Y is nickel.

10. A process in accordance with claim 8 wherein Y is cobalt.

11. A process in accordance with claim 2 wherein Q is silicon.

12. A hydrocarbon conversion process in accordance with claim 1 wherein said catalyst comprises said laminar 2:1 layer lattice aluminosilicate mineral having in addition a hydrogenation component deposited thereon.

13. A process in accordance with claim 12 wherein the hydrogenation component is at least one of the metals, metal oxides and metal sulfides from Groups VI and VIII.

14. A process according to claim 7 wherein said catalyst comprises said laminar 2:1 layer lattice aluminosilicate mineral having an addition a hydrogenation component deposited thereon, said deposited hydrogenation component comprising at least one of the metals, metal oxides and metal sulfides from Groups VI and VIII.

15. A process according to claim 8 wherein said catalyst comprises said laminar 2:1 layer lattice aluminosilicate mineral having in addition a hydrogenation component deposited thereon, said deposited hydrogenation component comprising at least one of the metals, metal oxides and metal sulfides from Groups VI and VIII.

16. A process according to claim 15 wherein the hydrogenation component is palladium.

17. A process in accordance with claim 12 wherein said hydrocarbon conversion process is hydrocracking a hydrocarbon charge stock under hydrocracking conditions.

18. A process according to claim 17, wherein the catalyst is the same as that defined in claim 13 and said catalyst is pre-reduced with hydrogen.

19. A process in accordance with claim 18 wherein said hydrocarbon conversion process is the hydrocracking of a hydrocarbon charge stock having a boiling range from 450° to 950° F. at atmospheric pressure.

20. A process in accordance with claim 19 wherein the hydrocarbon charge stock is a furnace oil boiling range material.

21. A process according to claim 18 wherein said hydrocarbon conversion process is the hydrocracking of a charge stock consisting of paraffinic hydrocarbons having from 4 to 8 carbon atoms.

22. A process according to claim 21 wherein the paraffinic hydrocarbon is a raffinate.

23. A process according to claim 19 wherein the catalyst is presulfided prior to use.

24. A process according to claim 23 wherein the hydrocracking conditions include a temperature from 300° to 750° F.

25. A process in accordance with claim 12 wherein said hydrocarbon conversion process is the hydroisomerization of at least one aliphatic hydrocarbon having from 4 to 7 carbon atoms per molecule under hydrosiomerization conditions.

26. A process according to claim 25 wherein the catalyst is the same as that defined in claim 13 and said catalyst is pre-reduced with hydrogen.

27. A process in accordance with claim 25 wherein the hydroisomerization conditions include a temperature from 300° F. to 750° F.

28. A process according to claim 26 wherein the hydrogenation component is selected from the group consisting of platinum and compounds thereof and palladium and compounds thereof.

29. A process according to claim 28 wherein Y is nickel.

30. A process for the preparation of 2,2-dimethylbutane which comprises contacting a charge stock consisting essentially of a mixture of hydrogen and normal hexane under hydroisomerization conditions in the presence of a catalyst comprising:

a laminar 2:1 layer-lattice aluminosilicate mineral possessing layer-lattice unit cells, each cell having an inherent negative charge balanced by cations exterior to said unit cell, and a hydrogenation component, said mineral corresponding to the following overall formula prior to drying and calcining:

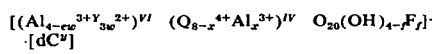

where

Al is aluminum;

Y is selected from the class consisting of nickel, cobalt and mixtures thereof;

Q is at least 0.95 mol fraction silicon ions, the remainder consisting of tetravalent ions having an ionic radius not to exceed 0.65 A; and F is fluorine;

C is at least one charge-balancing cation; and where e has a numerical value from 2 to 3 inclusive;

w has a numerical value from 0.01 to 2 inclusive, with the proviso that the quantity ew have a numerical value from 0.02 to 4 inclusive;

$f$ has a value of 4 or less;

x has a numerical value from 0.05 to 2.0 inclusive;

y is the valence of the cation C;

d is the number of cations C where the product $dy = x + 3(e-2)w$;

and wherein said first bracket represents said layer-lattice unit cell formulation and said second bracket represents said charge-balancing cations.

31. A process in accordance with claim 30 wherein the catalyst is presulfided before use.

32. A process in accordance with claim 31 where a sulfur compound is continuously added to the n-hexane charge stock.

33. A process in accordance with claim 30 wherein the hydroisomerization conditions include a temperature from 300° to 750° F.

34. A process for the production of liquid petroleum gas which comprises contacting a mixture of hydrogen and a raffinate boiling from 100° to 400° F. under hydrocracking conditions in the presence of a catalyst comprising:

a laminar 2:1 layer-lattice aluminosilicate mineral possessing layer-lattice unit cells, each cell having an inherent negative charge balanced by cations exterior to said unit cell, and a hydrogenation component, said mineral corresponding to the following overall formula prior to drying and calcining:

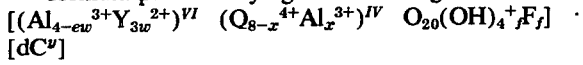

where

Al is aluminum;

Y is selected from the class consisting of nickel, cobalt and mixtures thereof;

Q is at least 0.95 mol fraction silicon ions, the remainder consisting of tetravalent ions having an ionic radius not to exceed 0.65 A; and F is fluorine;

C is at least one charge-balancing cation; and where e has a numerical value from 2 to 3 inclusive;

w has a numerical value from 0.01 to 2 inclusive, with the proviso that the quantity ew have a numerical value from 0.02 to 4 inclusive;

$f$ has a value of 4 or less;

x has a numerical value from 0.05 to 2.0 inclusive;

y is the valence of the cation C;

d is the number of cations C where the product $dy = x + 3(e-2)w$;

and wherein said first bracket represents said layer-lattice unit cell formulation and said second bracket represents said charge-balancing cations.

35. A process in accordance with claim 34 wherein the catalyst is presulfided prior to use.

36. A process for the preparation of isobutane, which comprises contacting a charge stock consisting essentially of hydrogen and normal hexane under hydrocracking conditions in the presence of a catalyst comprising:

a laminar 2:1 layer-lattice aluminosilicate mineral possessing layer-lattice unit cells, each cell having an inherent negative charge balanced by cations exterior to said unit cell, and a hydrogenation component;

said mineral corresponding to the following overall formula prior to drying and calcining:

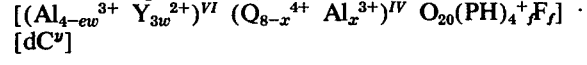

where

Al is aluminum;

Y is selected from the class consisting of nickel, cobalt and mixtures thereof;

Q is at least 0.95 mol fraction silicon ions, the remainder consisting of tetravalent ions having an ionic radius not to exceed 0.65 A; and F is fluorine;

C is at least one charge-balancing cation; and where e has a numerical value from 2 to 3 inclusive;

w has a numerical value from 0.01 to 2 inclusive, with the proviso that the quantity ew have a numerical value from 0.02 to 4 inclusive;

$f$ has a value of 4 or less;

x has a numerical value from 0.05 to 2.0 inclusive;

y is the valence of the cation C;

d is the number of cations C where the product $dy = x + 3(e-2)w$;

and wherein said first bracket represents said layer-lattice unit cell formulation and said second bracket represents said charge-balancing cations.

37. A process according to claim 36 wherein the catalyst is presulfided.

38. A process according to claim 36 wherein the catalyst is continually sulfided by having a sulfur compound present in the feedstock.

39. A process according to claim 36 wherein the hydrocracking conditions include a temperature from 350° to 1000° F., an LHSV of feedstock from 0.1 to 10.0, pressure from 400 to 3000 psig, and an $H_2$-to-feed mol ratio of 0.5 to 20.00.

40. A process for the desulfurization of a sulfur containing charge stock in the presence of hydrogen which comprises contacting a mixture of hydrogen and said sulfur containing charge stock under hydrodesulfurization conditions with a catalyst comprising:

a laminar 2:1 layer-lattice aluminosilicate mineral possessing layer-lattice unit cells, each cell having an inherent negative charge balanced by cations exterior to said unit cell, and a hydrogenation component comprising at least one of the metals, metal oxides or metal sulfides selected from the metals of Groups VI and VIII of the Periodic Table.

41. A process according to claim 40 wherein Q is silicon, Y is nickel, and the charge stock is a residual petroleum.

* * * * *

UNITED STATES PATENT AND TRADEMARK OFFICE
CERTIFICATE OF CORRECTION

PATENT NO. : 4,022,684
DATED : May 10, 1977
INVENTOR(S) : Edgar R. Black, Angelo A. Montagna and Harold E. Swift It is certified that error appears in the above-identified patent and that said Letters Patent are hereby corrected as shown below:

Col. 1, line 62
Col. 31, line 8
Col. 33, line 12
Col. 33, line 57
Col. 34, line 29

In each instance the formula should read as follows:

$$--[(Al^{3+}_{4-ew} Y^{2+}_{3w})^{VI} (Q^{4+}_{8-x} Al^{3+}_x)^{IV} O_{20}(OH)_{4-f}F_f] \cdot [dC^y]--$$

Col. 15, line 33, the formula should read: $--R_3 = Al^{IV}/Al^{VI}--$;

Col. 15, line 38, the formula should read:
$$-- x = 8R_3/R_1R_3 + R_1 + R_3 --;$$

Col. 20, line 43, add --450-- before "psig";

Col. 21, line 26, after "500°F." add -- to 900°F.--;

Col. 24, line 54, "500-1500 psig" should read --500-2500 psig--;

Col. 32, line 10, "an addition" should read --in addition--.

Signed and Sealed this

Twentieth Day of September 1977

[SEAL]

Attest:

RUTH C. MASON
Attesting Officer

LUTRELLE F. PARKER
Acting Commissioner of Patents and Trademarks